United States Patent
Kraus et al.

(10) Patent No.: US 9,370,529 B2
(45) Date of Patent: Jun. 21, 2016

(54) TANNIN INHIBITORS OF HIV

(71) Applicants: University of Iowa Research Foundation, Iowa City, IA (US); Iowa State University Research Foundation, Inc., Ames, IA (US)

(72) Inventors: George A. Kraus, Ames, IA (US); Wendy Maury, Coralville, IA (US)

(73) Assignees: University of Iowa Research Foundation, Iowa City, IA (US); Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 14/828,907

(22) Filed: Aug. 18, 2015

(65) Prior Publication Data

US 2016/0038520 A1 Feb. 11, 2016

Related U.S. Application Data

(62) Division of application No. 13/788,691, filed on Mar. 7, 2013, now Pat. No. 9,181,291.

(60) Provisional application No. 61/614,792, filed on Mar. 23, 2012.

(51) Int. Cl.
| | |
|---|---|
| *A61K 31/70* | (2006.01) |
| *A61K 31/365* | (2006.01) |
| *A61K 31/366* | (2006.01) |
| *A61K 31/22* | (2006.01) |

(52) U.S. Cl.
CPC .................. *A61K 31/70* (2013.01); *A61K 31/22* (2013.01); *A61K 31/365* (2013.01); *A61K 31/366* (2013.01)

(58) Field of Classification Search
None
See application file for complete search history.

(56) References Cited

U.S. PATENT DOCUMENTS

| | | | |
|---|---|---|---|
| 4,206,127 | A | 6/1980 | Woessner |
| 5,233,059 | A | 8/1993 | Larock |
| 2013/0252909 | A1 | 9/2013 | Kraus et al. |

OTHER PUBLICATIONS

Yoshoda et al., Chemical and Pharmaceutical Bulletin, 1996, 1436-1439.*
"U.S. Appl. No. 13/788,691, Final Office Action mailed Feb. 26, 2015", 14 pgs.
"U.S. Appl. No. 13/788,691, Non Final Office Action mailed Aug. 14, 2014", 13 pgs.
"U.S. Appl. No. 13/788,691, Notice of Allowance mailed Jun. 12, 2015", 7 pgs.
"U.S. Appl. No. 13/788,691, Preliminary Amendment filed Jun. 13, 2013", 3 pgs.
"U.S. Appl. No. 13/788,691, Response filed May 7, 2015 to Final Office Action mailed Feb. 26, 2015", 8 pgs.
"U.S. Appl. No. 13/788,691, Response filed Jul. 23, 2014 to Restriction Requirement mailed Jul. 2, 2014", 10 pgs.
"U.S. Appl. No. 13/788,691, Response filed Nov. 7, 2014 to Non Final Office Action mailed Aug. 14, 2014", 16 pgs.
"U.S. Appl. No. 13/788,691, Restriction Requirement mailed Jul. 2, 2014", 7 pgs.
Kim, et al., "Planta Medica", (2001), 277-279.
Orabi, Mohamaed, "New Monomeric and Dimeric Hydrolyzable Tannins From Tamarix Nilotica", Heterocycles vol. 80 No. 1 2010, (2010), 463-475.
Streitweiser, A, "Introduction to Organic Chemistry", Chapter 4, (1976).
Yoshida, et al., "Chemical and Pharmaceutical Bulletin", (1996), 1436-1439.

* cited by examiner

*Primary Examiner* — Traviss C McIntosh, III
(74) *Attorney, Agent, or Firm* — Schwegman Lundberg & Woessner, P.A.

(57) ABSTRACT

The invention provides a method to prevent or treat HIV-infection with synthetic tannins, and pharmaceutical compositions comprising synthetic tannins.

3 Claims, 3 Drawing Sheets

TANNIN INHIBITORS OF HIV

CROSS-REFERENCE TO RELATED APPLICATIONS

This application is a divisional of U.S. application Ser. No. 13/788,691, filed on Mar. 7, 2013, and published as U.S. 2013-0252909 on Sep. 26, 2013, which claims priority of U.S. Provisional Patent Application Ser. No. 61/614,792, filed Mar. 23, 2012, which is incorporated by reference herein.

GOVERNMENT GRANT SUPPORT

This invention was made with the Support of Grant No. P50 AT004155, awarded by the National Institutes of Health. The U.S. Government has certain rights in the invention.

BACKGROUND OF THE INVENTION

With more than 33 million people currently infected with human immunodeficiency virus (HIV) and 2 million additional individuals infected each year, there is a worldwide imperative to reduce transmission of this deadly virus. Worldwide, sexual transmission is the primary route of new virus infections. Strategies to reduce spread of this virus can be achieved by reducing virus loads in currently infected individuals (and thereby reducing levels of virus exposure) and/or by blocking sexual transmission by the use of effective and safe microbicides.

Clinically useful anti-retrovirals target a number of steps of the HIV-1 life cycle including co-receptor (CCR5) binding, virus membrane/cellular membrane fusion, reverse transcription, integration and proteolytic processing. See, e.g., Martins et al., *Curr. Med. Chem.*, 15, 1083 (2008). Combination therapy regiments have proved highly efficacious at controlling HIV-1 load in most infected individuals. Nonetheless, drug resistant HIV-1s arise and are transmitted between individuals, reducing the efficacy of currently available antivirals. See, e.g., A. M. Wensing et al., *Antviral Res.*, 85, 59 (2010); S. Broder, *Antiviral Res.*, 85, 1 (2010); and J. A. Este et al., *Antiviral Res.*, 85, 25 (2010). Additionally, some of the HIV antivirals have significant off target effects that result in cytotoxicity, and many of these antivirals are expensive, thereby decreasing their attractiveness as daily use microbicides through the world and limiting their use as antivirals in developing countries. There remains a need for additional non-toxic HIV microbicides as well as antiviral therapies that can be broadly and safely used.

The mint family (Lamiaceae) produces a wide variety of constituents with medicinal properties. Several family members have been reported to have antiviral activity, including lemon balm (*Melissa officinalis* L.), sage (*Salvia* spp.), peppermint (*Mentha* x *piperita* L.), hyssop (*Hyssopus officinalis* L.), basil (*Ocimum* spp.) and self-heal (*Prunella vulgaris* L.).

The mint (Lamiaceae) family member, *Prunella vulgaris*, or "self-heal" has been evaluated by the Iowa Center for Botanical Dietary Supplements for anti-HIV activity. Water- and ethanol-based extracts were tested for their ability to inhibit HIV-1 infection. Aqueous extracts displayed potent anti-retroviral activity against HIV-1 at sub µg/mL concentrations with little to no cellular cytotoxicity at concentrations more than 100-fold higher. Time-of-addition studies demonstrated that aqueous extracts were effective when added during the first five hours following initiation of infection, suggesting that the botanical constituents were targeting entry events. Further analysis revealed that extracts inhibited both virus/cell interactions and post-binding events. While only 40% inhibition was maximally achieved in virus/cell interaction studies, extracts effectively blocked post-binding events at concentrations similar to those that blocked infection, suggesting that the extracts were most effective at targeting post-binding entry events. See, C. Oh et al., *Virology J.*, 8, 188 (2011).

However, the structures of the compounds responsible for this bioactivity have not been determined. Therefore, a continuing need exists for purified, well-characterized compounds with potent anti-HIV activity and good therapeutic indices. Antivirals targeting early steps within the HIV life cycle such as receptor binding or fusion events may be particularly attractive HIV inhibitors since these agents block the initiation of the infectious cycle, thereby preventing virus entry into the host cell.

SUMMARY OF THE INVENTION

The present invention provides a method for treating HIV infection comprising administering to a subject, such as a human or susceptible animal, afflicted with HIV infection, including infection with R5 and X4 viral strains, an effective anti-HIV amount of a tannin compound of formula (I):

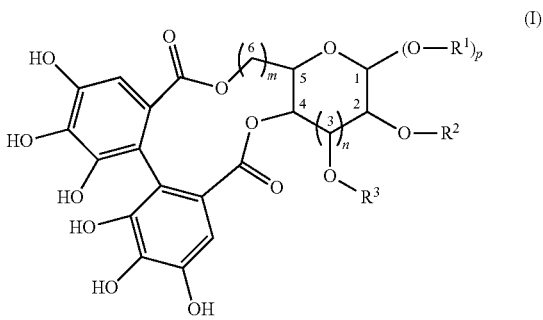

wherein $R^1$, $R^2$, and $R^3$ are individually H, $(C_1-C_4)$alkyl or galloyl (G), p is 0 or 1, m is 0 or 1, and n is 0 or 1, with the proviso that when n is 0 there is a single bond between $C_2$ and $C_4$; and when p is O, $C_1$ is $CH_2$. The present invention also provides novel compounds of formula (I) and compositions such as medicaments comprising them, in combination with carriers such as pharmaceutically acceptable vehicles.

In one embodiment of the invention n is 1, m is 1 and p is 1. In one embodiment of the invention at least one of $R^1$, $R^2$ and $R^3$ is G. In one embodiment of the invention $R^1$ is $CH_3$, H or galloyl. In one embodiment of the invention $R^2$ and/or $R^3$ are G or H. In one embodiment of the invention $R^1$ is G and/or $R^2$ and/or $R^3$ are H or G, for example, $R^2$ and $R^3$ are H or $R^2$ and $R^3$ are G. Although the substituents at positions 1-5 of the pyran ring can be a or α or β to the plane of the ring, in one embodiment of the invention the pyran moiety in formula (I):

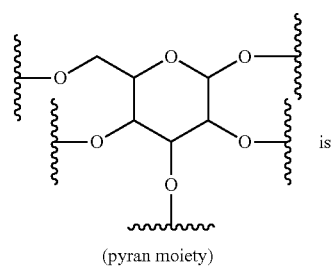

(pyran moiety)

-continued

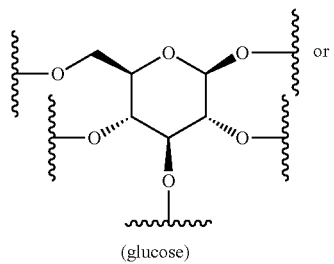
(glucose)

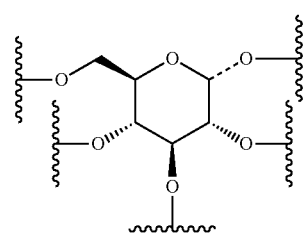
(mannose) [labeled (Ib) in source — actually the second glucose variant]

The pyran moiety of formula (I):

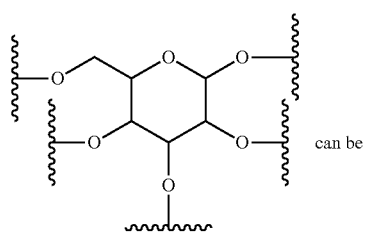 can be

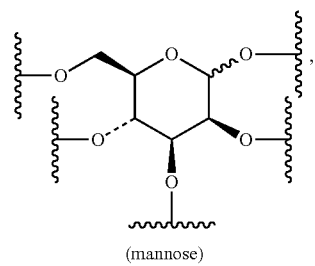
(mannose)

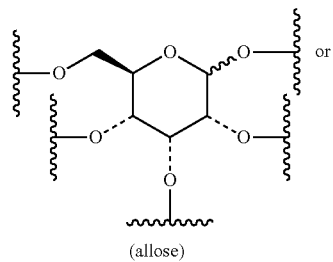
(allose)

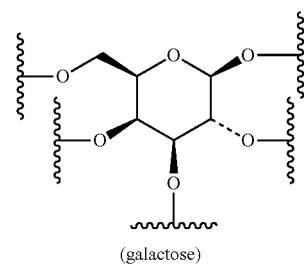
(galactose)

wherein a waved line ( ) indicates that the attached substituent can be in the alpha (------) or beta ( ▬▬ ) configuration or can be any combination thereof. For example in Ic and Id, the 1-substituent can be alpha-methoxy, alpha-OG or beta-OG. Representative compounds comprising a methoxy or galloyloxy group at $C_1$ are depicted below:

IA

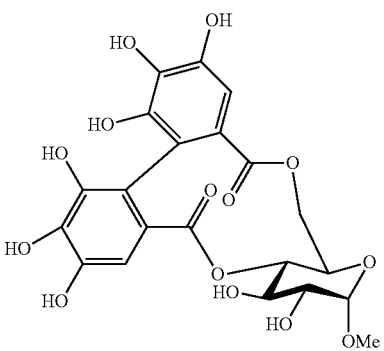

IB

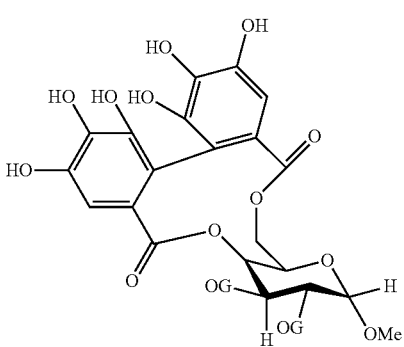

IC

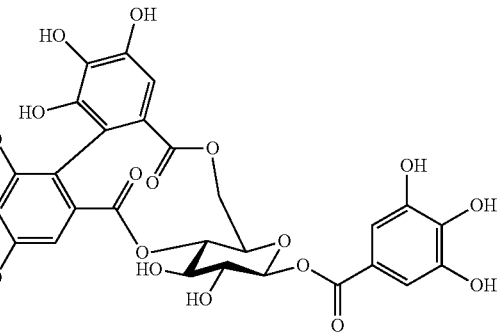

ID

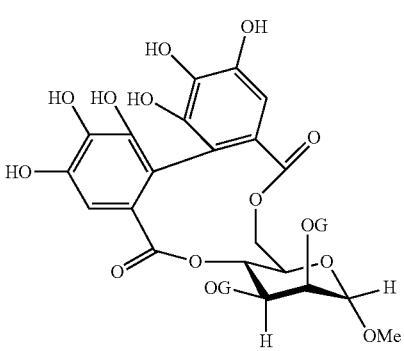

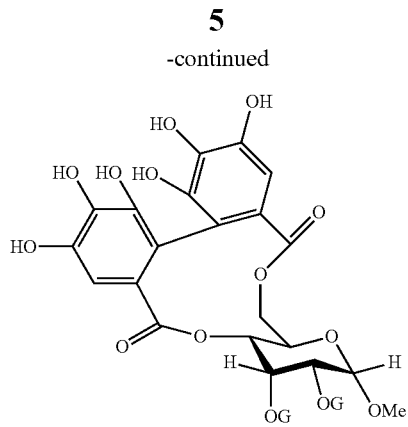

(IE)

In the embodiment of the invention wherein n is 0, the furan moiety of formula (I):

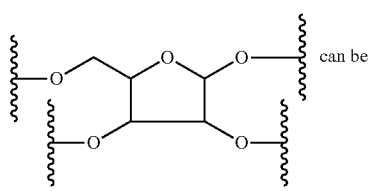

can be (If)

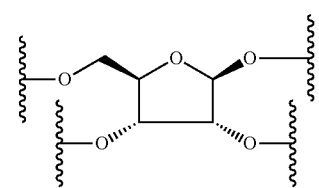

(ribose)

(Ig)

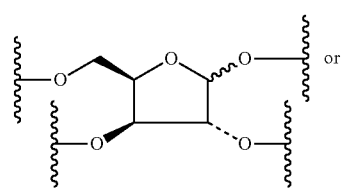

or (xylose)

(Ih)

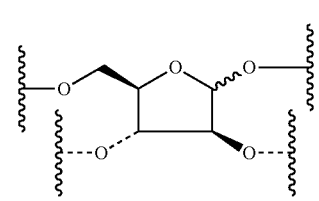

(arabinose)

In this embodiment of the invention R$^1$ or R$^2$ can be CH$_3$. In another embodiment R$^1$ and/or R$^2$ can be G.

In a further embodiment of the invention n is 1, m is 0 and p is 0. In this embodiment, the pyran moiety of formula (I):

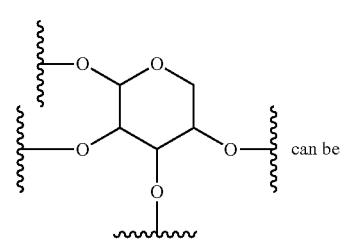

can be (Ii)

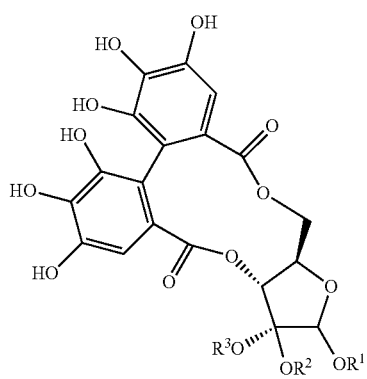

or (lyxose)

(Ij)

(arabinopyranose)

In this embodiment, R$^2$ and R$^3$ can be G. In another embodiment of this invention R$^2$ or R$^3$ can be CH$_3$.

The present invention also provides a method for treating HIV infection comprising administering to a subject afflicted with HIV an effective anti-HIV amount of a compound of formula (II):

(II)

wherein R$^1$, R$^2$ and R$^3$ are individually H, (C$_1$-C$_4$)alkyl or galloyl (G), preferably wherein at least one of R$^1$, R$^2$ or R$^3$ is G.

In formula (II) R$^2$ can be G and R$^1$ and/or R$^3$ can be H. In formula (II), R$^3$ can be G, R$^2$ can be H and R$^1$ can be (C$_1$-C$_4$) alkyl, e.g., CH$_3$. Novel compounds of formula (II) and compositions such as medicaments comprising them are also an aspect of the present invention.

The present invention further provides a method for treating HIV infection comprising administering to a subject afflicted with HIV infection an anti-HIV amount of a compound of formula (III):

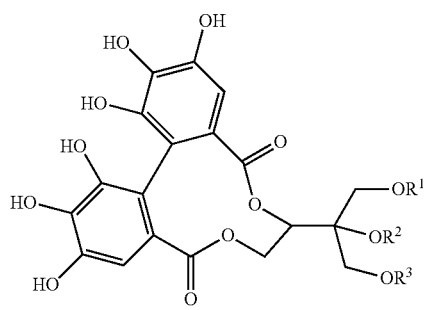

(III)

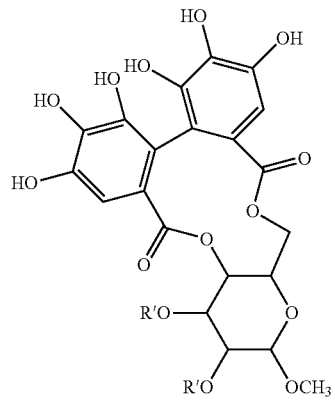

I(B)

wherein $R^1$, $R^2$ and $R^3$ are individually H, $(C_1-C_4)$alkyl or galloyl (G), preferably wherein at least one of $R^1$, $R^2$ or $R^3$ is G. For example, $R^1$ and/or $R^3$ can be G, and/or $R^2$ can be H.

The present invention provides novel synthetic tannins as well as the use of known tannins to inhibit HIV, preferably with little associated toxicity. Preliminary studies suggest that these tannins inhibit one or more entry events during the HIV life cycle. Development of additional anti-retroviral therapies (ART) against these early steps in the HIV life cycle are valuable since the two current HIV entry in therapies (CCR5 and fusion inhibitors) have sufficient drawbacks that they are only used as salvage therapies. Thus, as used herein, the terms "treat" or "treatment" with the compounds of the invention includes their use in prophylaxis, e.g., blocking or inhibiting initial or further HIV infectivity of mammalian, e.g., human cells, such as binding to or entry thereinto, as well as counteracting active infection and/or one or more symptoms of HIV infection or of HIV-AIDs. Additionally, the large therapeutic or "safety" index (cytotoxicity/antiviral activity) of the present compounds suggests that these tannins may serve not only as anti-retrovirals, but as HIV microbicides as well.

Therefore, compounds of formula (I) useful in the present method include:

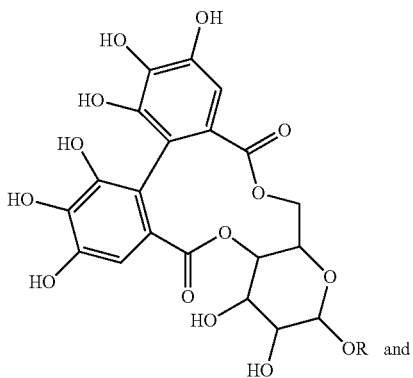

I(A)

wherein R is H, galloyl or $CH_3$, and $R^1$ is H or galloyl.

Compounds of formula (I) and (II) generally fall within the class of hydrolyzable tannins known as ellagitannins Preferably the pyran moiety of a tannin compound of formula (I), e.g., IA or IB, is the moiety 1(b) as shown above. Some of the tannin compounds useful in the present invention have previously been characterized, but were not known to be useful against HIV/AIDS. For example, the novel compounds of formula (I) do not per se include the compound I(A), strictinin, which comprises a pyran moiety (Ia) derived from glucose, and do not per se include the compound of formula (I) wherein the pyran moiety is (Ia), n, p and m are 1, $R^1$ is H and $R^2$ and $R^3$ are G (tellimagrandin) or wherein $R^1$, $R^2$ and $R^3$ are all G (eugeniin) See R. Saha et al., *Antiviral Res.*, 88, 90 (2010) and S. Tamura, *Biorg. & Med. Chem. Lett.*, 20, 1598 (2010).

Furthermore, it is believed that the compounds of the invention will exhibit microbiocidal activity.

DETAILED DESCRIPTION OF THE INVENTION

Figure 1:
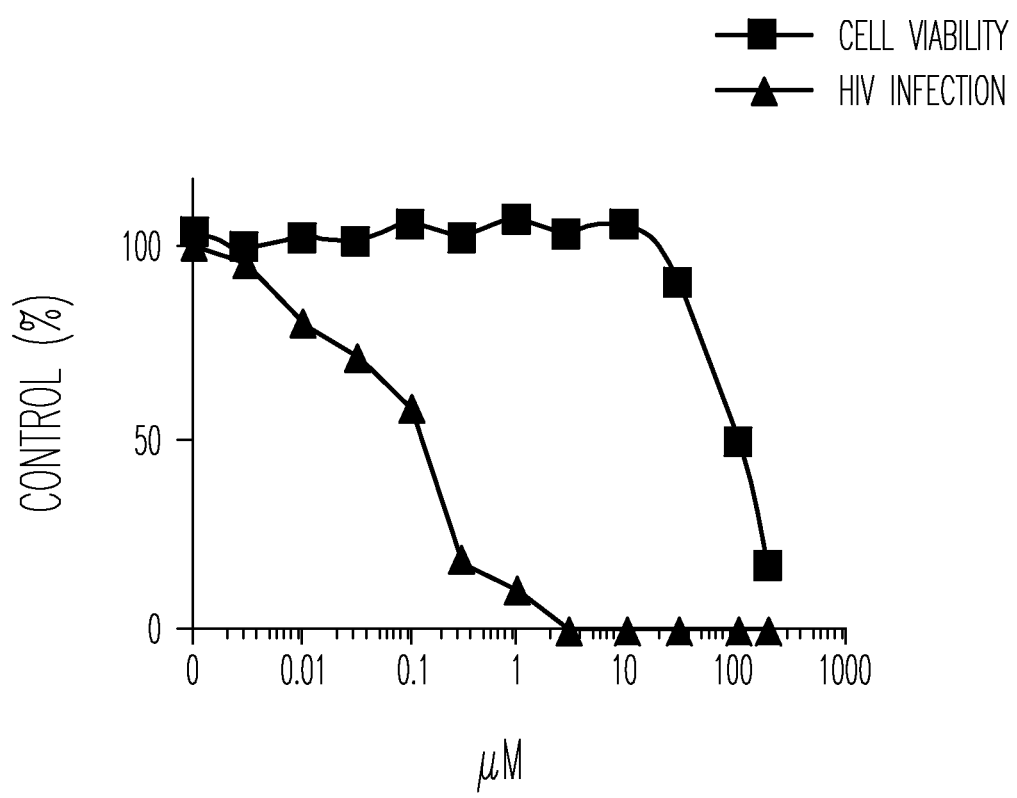
FIGS. 1 and 2. Dose response curve for inhibition of CXCR4 tropic HIV NL4-3 (triangles), CCR5 tropic HIV AD8 (diamonds) and HeLa 37 cell cytotoxicity (squares) for the tannins IA (FIG. 1) and IB (FIG. 2). Data points shown represent the means and standard errors of data from three independent experiments performed in triplicate.

Suitable methods for preparing compounds of formula (I), (II) and/or (III) are described below on Schemes 1, 2, 3, 4, 5. 6, 7 or 8. The group G is 3,4,5-trihydroxybenzoyl, the group Bn is benyzl; TBG is tri-O-benzylgalloyl, OMOM is methoxymethoxy.

It will be appreciated that the esterification reactions shown on Schemes 1 and 2 may require the use of, or conveniently may be applied to, starting materials having protected functional groups, and deprotection is required as an intermediate or final step to yield the desired compound. Protection and deprotection of functional groups may be affected using conventional means. Thus, for example, hydroxyl groups may be protected using any conventional hydroxyl protecting group, for example, as described in "Protective Groups in Organic Chemistry," Ed. J. F. W. McOmie (Plenum Press, 1973) or "Protective Groups in Organic Synthesis" by Theodora W. Greene (John Wiley and Sons, 1981). Examples of suitable hydroxyl protecting groups includes groups selected from alkyl (e.g., methyl, t-butyl or methoxymethyl), aralkyl (e.g., benyl, diphenylmethyl or triphenylmethyl), heterocyclic groups such as tetrahydropyranyl, acyl (e.g., acetyl or benzoyl) and silyl groups such as trialkylsilyl (e.g., t-butyldimethylsilyl). The hydroxyl protecting groups may be removed by conventional techniques. Thus, for example, alkyl, silyl, acyl and heterocyclic groups may be removed by solvolysis, e.g., by hydrolysis under acidic or basic conditions. Aralkyl groups such as benzyl may be cleaved by hydrogenolysis in the presence of a noble metal catalyst such as palladium-on-charcoal. Silyl groups may also conveniently be removed using a source of fluoride ions such as tetra-n-butylammonium fluoride.

Pharmaceutically-acceptable salts of the compounds of formulas (I)-(III) are also within the scope of the invention as are novel intermediates useful to prepare the compounds of formulas (I)-(III). If the configuration (α- or β-) or a substituent is not indicated, the configuration can be racemic or comprise either isomer in any amount.

Scheme 1

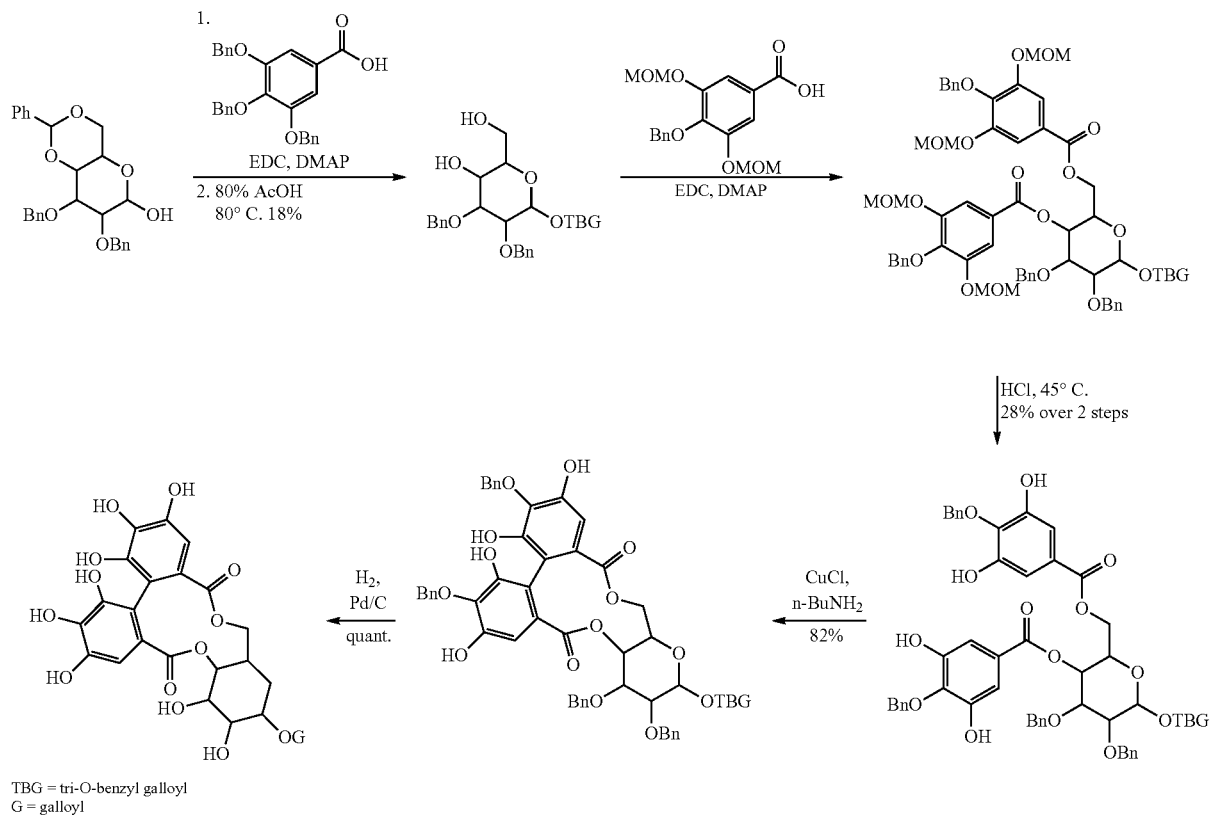

TBG = tri-O-benzyl galloyl
G = galloyl

Scheme 2

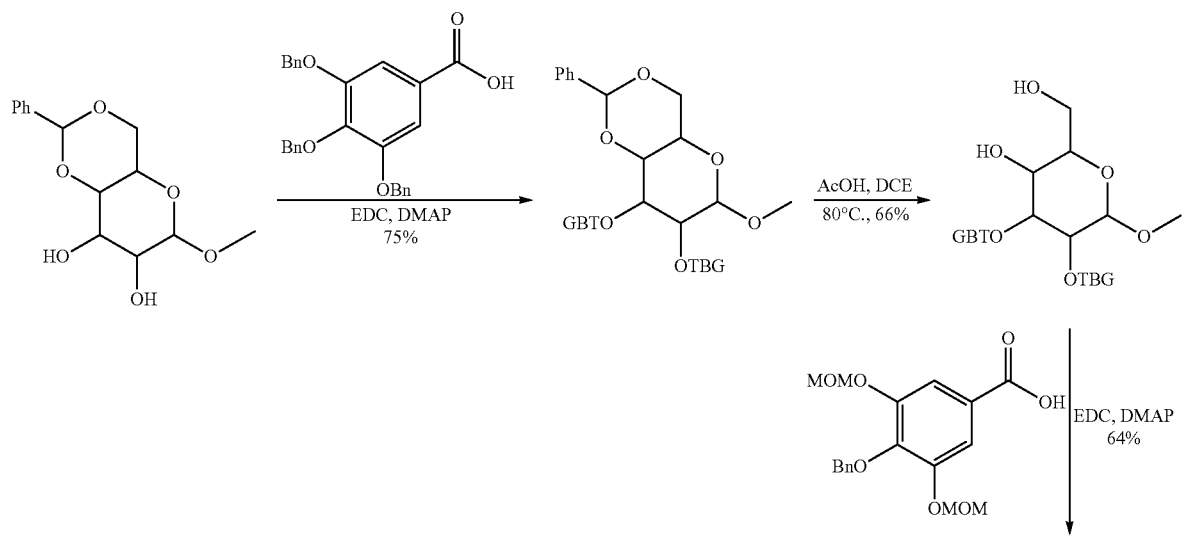

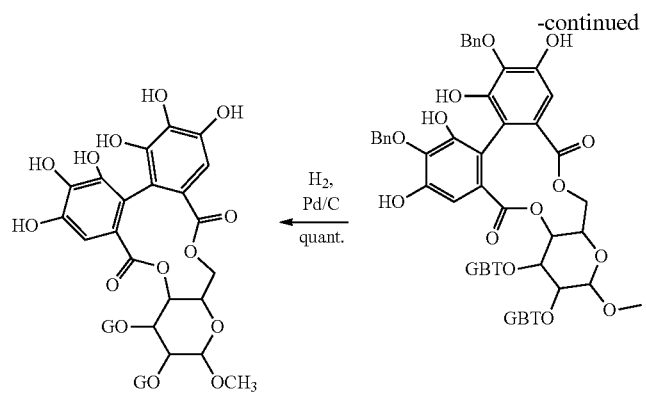
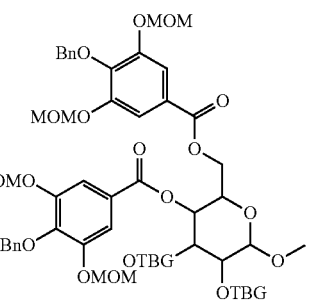
The preparation of compound IA and IB is summarized on Schemes 3 and 4, below:
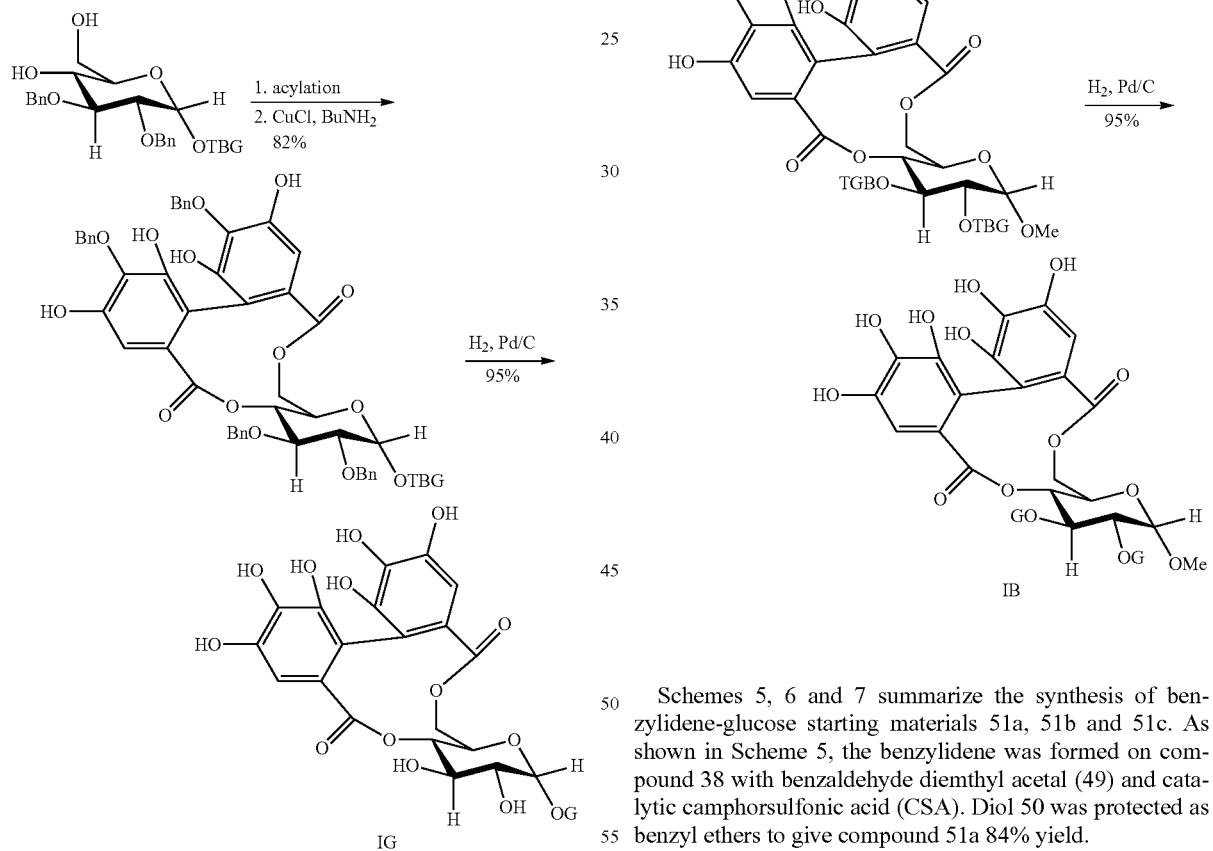
Schemes 5, 6 and 7 summarize the synthesis of benzylidene-glucose starting materials 51a, 51b and 51c. As shown in Scheme 5, the benzylidene was formed on compound 38 with benzaldehyde diemthyl acetal (49) and catalytic camphorsulfonic acid (CSA). Diol 50 was protected as benzyl ethers to give compound 51a 84% yield.
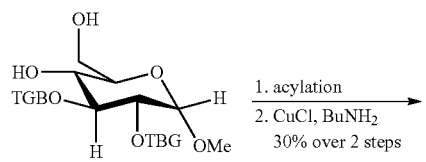
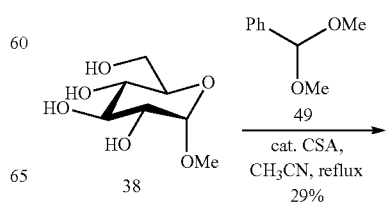

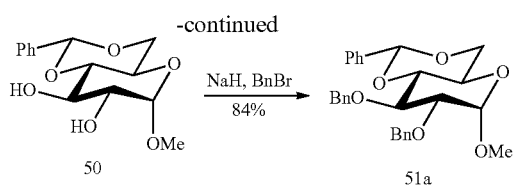

As shown in Scheme 6, starting with α,β-D-glucose pentaacetate (57), bromo substitution at the anomeric position with HBr in AcOH, followed by nucleophillic displacement with benzyl alcohol afforded β-compound 58. The acetate groups were deprotected with sodium methoxide to give tetraol 59, which upon treatment with 49 was converted to compound 60. The hydroxyl groups were protected as benzyl eithers under standard conditions of sodium hydride and benzyl bromide to yield 51b in 62% yield.

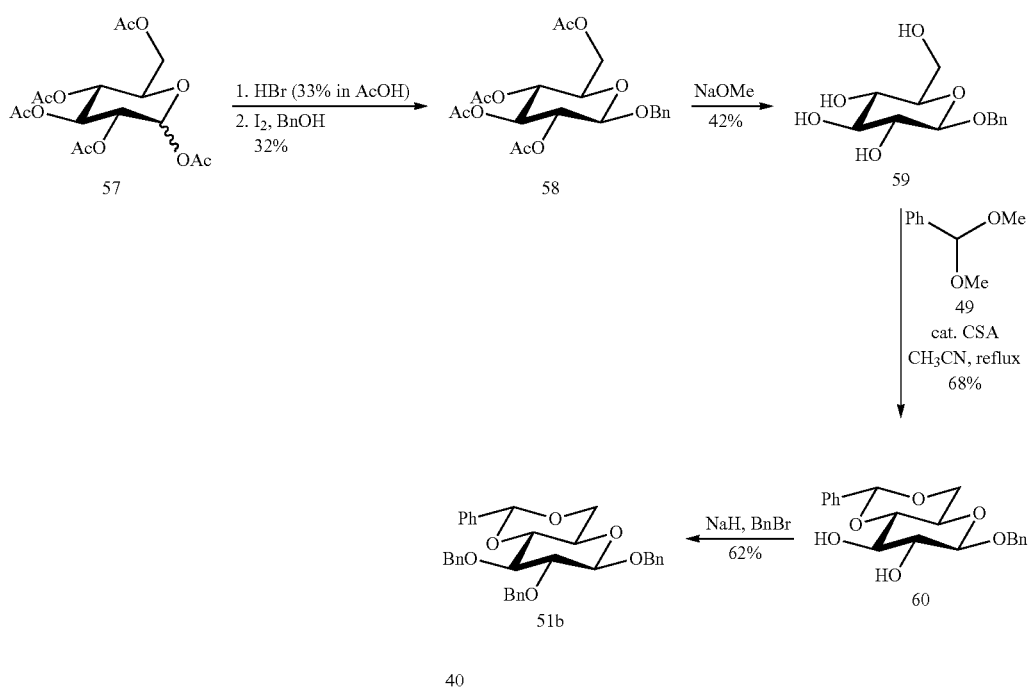

As shown in Scheme 7, starting with allyl gluco-pyranoside 61, benzylidene 64 was synthesized using 49 and catalytic amounts of CSA. Protection of the remaining alcohols as benzyl ethers afforded dibenzyl protected 63. The O-allyl group was removed under stoichiometric $PdCl_2$ and sodium acetate in acetic acid. The hydroxy group on compound 64 was esterified with acid 12 to give a mixture of α,β-diastereomers 51c and 51d. The two diastereomers were separated by column chromatography to yield pure 51c and 51d.

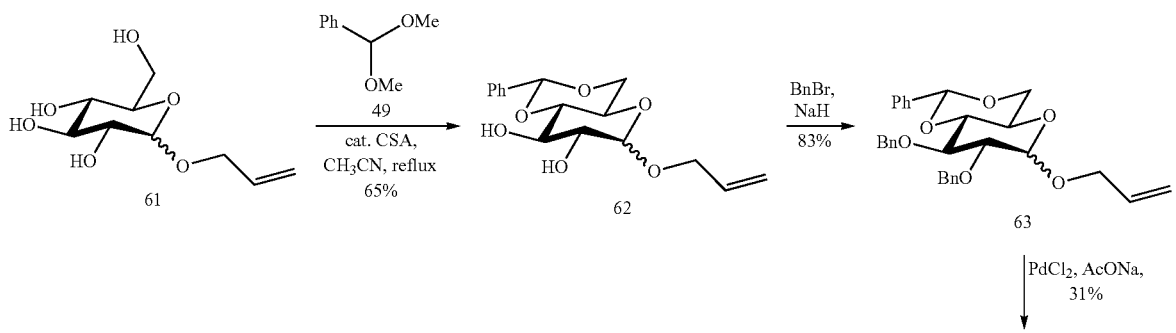

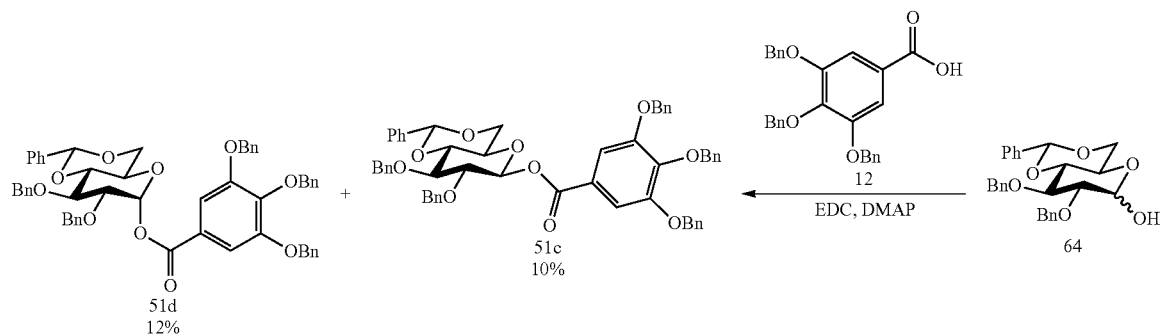

After isolating compounds 51a-c, the HHDP diphenyl moiety was installed following the pathway describe previously for 56a (Scheme 8). Benzylidene deprotection with acetic acid at 80° C. proceeded smoothly for 51b, but compounds 51c required addition of dichloroethane as a cosolvent due to starting material insolubility. Diols 52a-c were coupled to compound 19 to form products 53a-c. Then, the oxidative coupling precursors Ma-c were generated from deprotection of the MOM-ethers with HCl. Oxidative coupling was effective for 54a and 54b but compound 54c was insoluble in the reaction solvent, methanol. However, addition of dichloromethane as a co-solvent circumvented this problem and afforded the oxidative coupling product 55c in good yields. All of the HHDP-containing compounds were made as a single atropisomer by this method. The compounds were subjected to hydrogenolysis conditions to remove the benzyl ethers to afford ellagitannis IA, IB, IC, IF and IG.

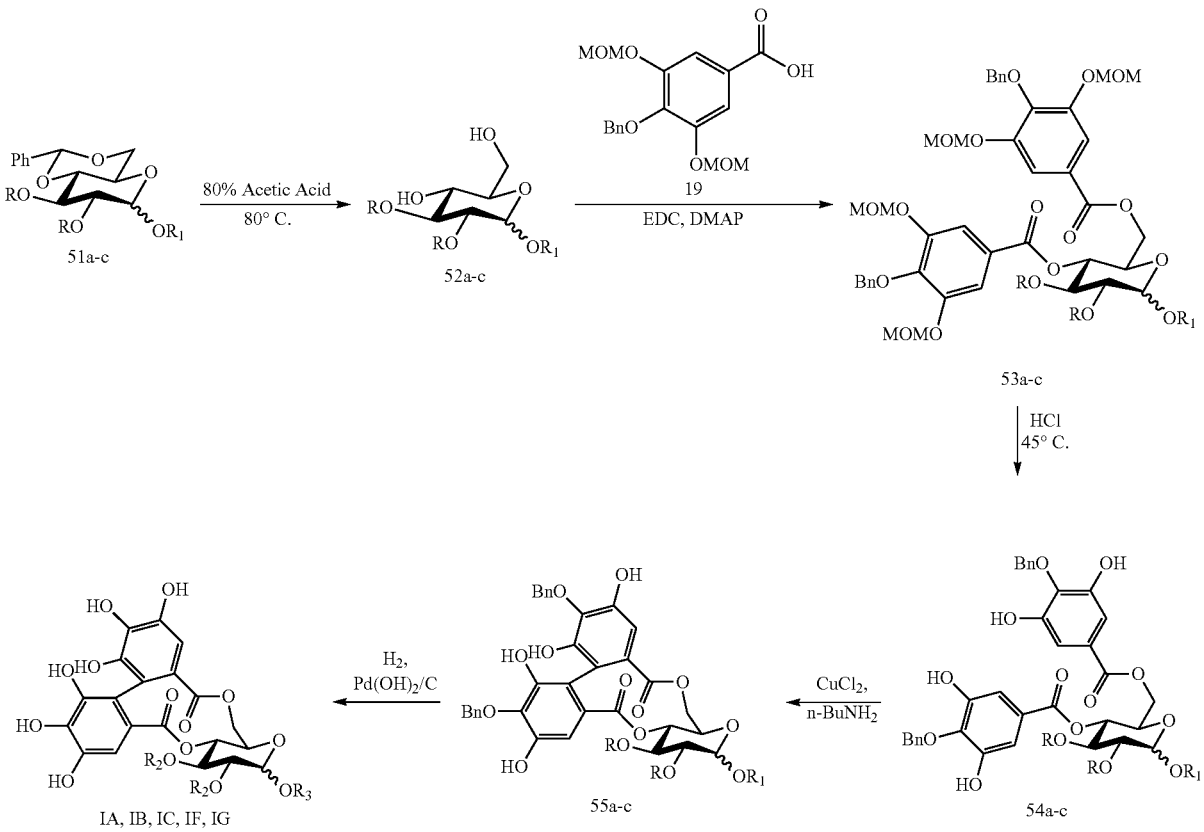

The structures shown in Scheme 8 and the yields are summarized on Table 1, below, wherein OTBG=3,4,5-O-benzylgalloyloxy.

TABLE 1

| SM | OR | $OR_1$ | Yield (%) 51 | Yield (%) 52 | Yield (%) 53 | Yield (%) 54 | Pdt. | $OR_2$ | $OR_3$ |
|---|---|---|---|---|---|---|---|---|---|
| 51a | OBn | α-OMe | 78 | 85 | 68 | 62 | IA | OH | α-OMe |
| 51e | O-galloyl | α-OMe | 85 | 81 | 70 | 40 | IB | O-galloyl | α-OMe |
| 51c | OBn | β-OTBG | 70 | 77 | 85 | 52 | IC | OH | β-G |
| 51b | OBn | β-OBn | 76 | 60 | 75 | 44 | IF | OH | α/β-OH |
| 51d | OBn | α-OTBG | 73 | 73 | 75 | 64 | IG | OH | α-G |

The synthesis of one embodiment of the compounds of formula II, IIB is summarized on Scheme 9, below:

Scheme 9

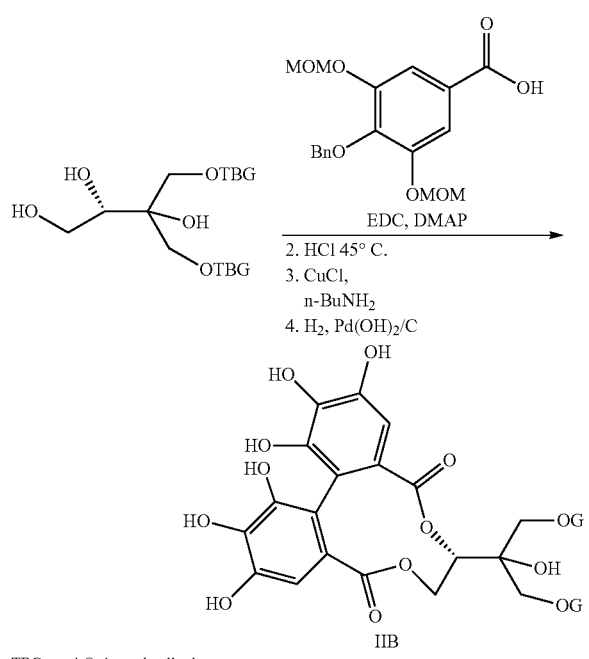

TBG = tri-O- benzyl galloyl
G = galloyl

Examples

I. Synthesis of Tannins

Compounds of formula (I)-(III) can be prepared by the general methodologies shown for the synthesis of IA and IB as shown on Schemes 1 and 2, respectively.

A. Steglich Esterification:

In a round bottom flask, 1-ethyl-3-(3-dimethylaminopropyl)carbodiimide hydrochloride (3 equiv), N,N-4-dimethylaminopyridine (3.5 equiv), and acid (1.25 equiv) were added to the alcohol in methylene chloride. The reaction was stirred at rt for 3 hours. When the reaction was complete 1 M phosphoric acid was added and the organic layer was extracted with methylene chloride. The organic layer was washed with 1 M phosphoric acid, water and brine, dried over $MgSO_4$, filtered and evaporated in vacuo. The crude product was then purified by column chromatography.

B. Benzylidene Deprotection

In a round bottom flask, the benzylidene compound was heated in 80% acetic acid to 80° C. for 2 h. (Dichloroethane was added if the compound was insoluble at 80° C.) Upon completion the reaction was extracted with $CH_2Cl_2$, washed with $NaHCO_3$(sat.) until neutral pH, water and brine, dried over $MgSO_4$, filtered and evaporated in vacuo. The crude product was purified by column chromatography.

C. Methoxymethyl Group Deprotection

To a stirred solution of methoxymethyl-protected phenol in 2-propanol (80% volume) and THF (20% volume), was added conc. HCl (0.01 M). The mixture was stirred for 12 h at 45° C. Sat. $NaHCO_3$ was added until the reaction reached neutral pH. Evaporated in vacuo. The mixture was extracted with ethyl acetate, washed with water and brine, dried over $MgSO_4$, filtered and evaporated in vacuo. The crude product was then purified by column chromatography.

D. Copper Coupling

To a stirred solution of $CuCl_2$ (5 equiv) in methanol was added n-butylamine (20 equiv) at rt. The mixture was stirred for 30 min at this temperature. The phenol in methanol was added and the reaction mixture was stirred at rt for 20 min. The reaction was quenched with 4 M HCl and extracted with ethyl acetate. Washed with 1 M HCl, sat. $NaHCO_3$, and then brine, dried over $MgSO_4$, filtered and evaporated in vacuo. The crude product was then purified by column chromatography.

E. Hydrogenolysis

To a stirred solution of 1 in methanol and THF was added 10% Pd/C (10% by weight). The flask was evacuated and filled with $H_2$, this process was repeated three times. The reaction was stirred under a $H_2$ atmosphere for 12 h. Upon competition, the reaction mixture was filtered through a pad of celite and evaporated in vacuo to furnish the desired product.

The spectroscopic characterization of certain compounds of the invention is provided on Table 2, below:

TABLE 2

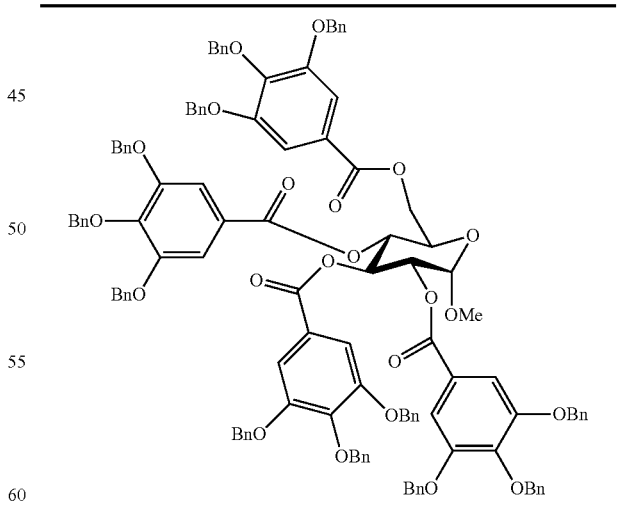

(2S,3R,4S,5R,6R)-2-methoxy-6-(((3,4,5-tris(benzyloxy)benzoyl)oxy)methyl)
tetrahydro-2H-pyran-3,4,5-triyl tris(3,4,5-tris(benzyloxy)benzoate) (35). $^1$H NMR (300 MHz, $CDCl_3$) δ 3.59 (s, 3 H), 4.13 (br, 1 H), 4.49 (t, J = 12.9 Hz, 2 H), 4.90-5.21 (m, 24 H), 5.42 (t, 3 Hz, 1 H), 5.77 (dt, J = 9.6 Hz, 3.3 Hz, 1 H), 6.07 (d, J = 6.6 Hz, 1 H), 6.27 (dt, J = 10.2 Hz, 3.3 Hz 1 H), 6.96-7.52 (m, 68 H).

TABLE 2-continued

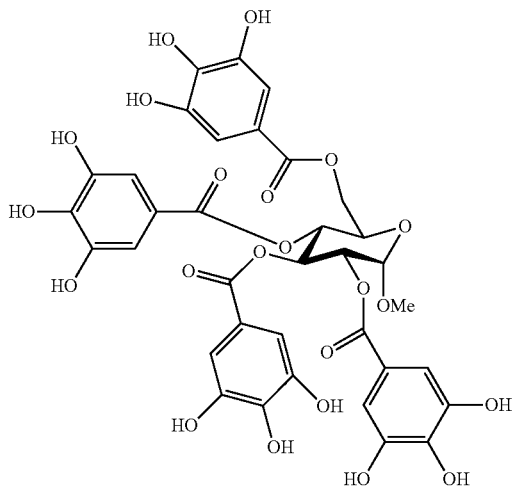

(2S,3R,4S,5R,6R)-2-methoxy-6-(((3,4,5-trihydroxybenzoyl)oxy)methyl) tetrahydro-2H-pyran-3,4,5-triyl tris(3,4,5-trihydroxybenzoate) (36). $^1$H NMR (300 MHz, COCD$_6$) δ 3.50 (s, 3 H), 4.21 (br, 1 H), 4.37 (m, 2 H), 4.50 (d, J = 12.9 Hz, 1 H), 5.20 (m, 1 H), 5.55 (t, J = 9.3 Hz, 1 H), 6.02 (t, J = 9.6 Hz, 1 H), 6.70 (s, 2 H), 7.00 (s, 2 H), 7.07 (s, 2 H), 7.21 (s, 2 H)

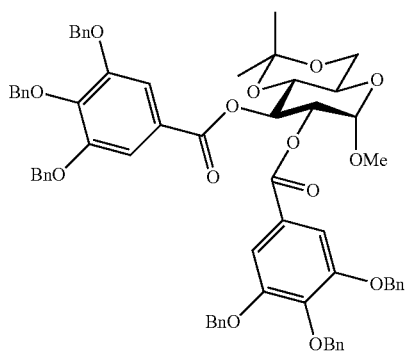

(4aR,6S,7R,8S,8aR)-6-methoxy-2,2-dimethylhexahydropyrano[3,2-d][1,3]dioxine-7,8-diyl bis(3,4,5-tris(benzyloxy)benzoate) (41). $^1$H NMR (300 MHz, CDCl$_3$) δ 1.40 (s, 3 H), 1.50 (s, 3 H), 3.43 (s, 3 H), 3.86-4.00 (m, 4 H), 3.89 (m, 13 H), 5.21 (d, J = 3.0 Hz, 1 H), 5.85 (t, J = 10.2 Hz, 1 H), 7.18-7.45 (m, 34 H).

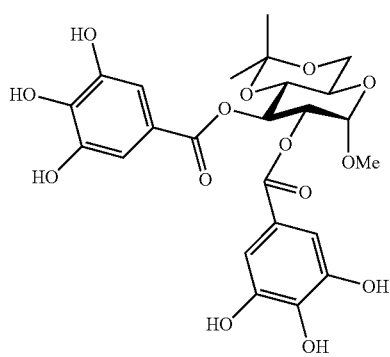

(4aR,6S,7R,8S,8aR)-6-methoxy-2,2-dimethylhexahydropyrano[3,2-d][1,3]dioxine-7,8-diyl bis(3,4,5-trihydroxybenzoate) (42). $^1$H NMR (300 MHz, COCD$_6$) δ 1.29 (s, 3 H), 1.51 (s, 3 H), 3.40 (s, 3 H), 3.63 (t, J = 6.6 Hz, 1 H), 3.73-3.90 (m, 3 H), 5.05-5.11 (m, 2 H), 5.69 (t, J = 9.6 H, 1 H), 7.04 (s, 2 H), 7.07 (s, 2 H).

TABLE 2-continued

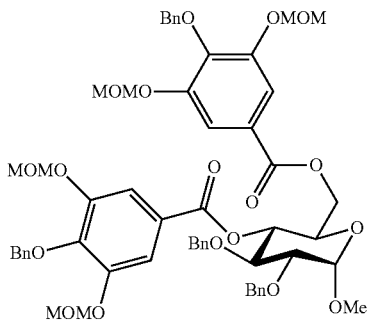

(2R,3R,4S,5R,6S)-4,5-bis(benzyloxy)-2-(((4-(benzyloxy)-3,5-bis(methoxymethoxy)benzoyl)oxy)methyl)-6-methoxytetrahydro-2H-pyran-3-yl 4-(benzyloxy)-3,5-bis (methoxymethoxy)benzoate (53). $^1$H NMR (300 MHz, CDCl$_3$) δ 3.46 (s, 9 H), 3.47 (s, 6 H), 3.66 (dd, J = 9.3 Hz, J = 3.6 Hz, 1 H), 4.07-4.31 (m, 4 H), 4.46 (d, 11.7 Hz, 1 H), 4.67 (m, 3 H), 4.83 (d, J = 8.1 Hz, 1 H), 4.87 (d, J = 7.5 Hz, 1 H), 5.13-5.27 (m, 14 H), 7.13-7.53 (m, 22 H) $^{13}$C NMR (75 MHz, CDCl$_3$) δ 56.37, 56.30(4), 63.64, 67.75, 71.27, 73.48, 75.14, 75.19, 75.51, 79.20, 79.57, 95.41(4), 98.04, 112.1(4), 122.2(2), 124.9, 125.2, 127.4-128.5(20), 137.2, 137.3, 138.0, 138.2, 150.9(4), 164.7, 164.5.

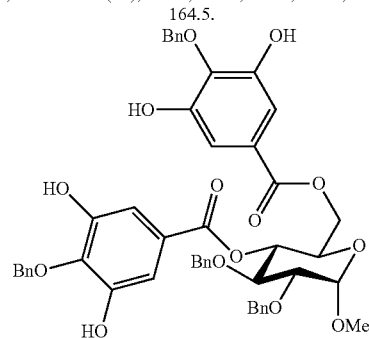

(2R,3R,4S,5R,6S)-4,5-bis(benzyloxy)-2-(((4-(benzyloxy)-3,5-dihydroxybenzoyl)oxy)methyl)-6-methoxytetrahydro-2H-pyran-3-yl 4-(benzyloxy)-3,5-dihydroxybenzoate (54). $^1$H NMR (300 MHz, CDCl$_3$) δ 3.42 (s, 3 H), 3.70 (dd, J = 6.3 Hz, 3.6 Hz, 1 H), 4.06 (m, 2 H), 4.30 (J = 7.5 Hz, 1 H), 4.54 (dd, J = 9.3 Hz, J = 3.0 Hz, 1 H), 4.60-4.67 (m, 3 H), 4.79 (d, J = 5.4 Hz, 1 H), 4.82 (d, J = 5.4 Hz, 1 H), 5.10 (d, J = 8.1 Hz, 4 H), 5.29 (t, J = 7.5 Hz, 1 H), 6.08 (br, 4 H), 7.05-7.36 (m, 24 H) $^{13}$C NMR (75 MHz, CDCl$_3$) δ 55.65, 60.82, 63.21, 67.64, 71.02, 73.86, 75.23, 75.29, 75.59, 79.03, 79.91, 99.39, 110.1(4), 124.7, 125.0, 127.6-128.9(20), 136.8(2), 138.0(3), 149.2(4), 165.7, 166.6.

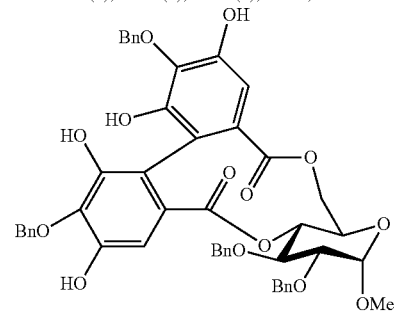

(11aR,13S,14R,15S,15aR)-3,6,14,15-tetrakis(benzyloxy)-2,4,5,7-tetrahydroxy-13-methoxy-11,11a,13,14,15,15a-hexahydrodibenzo[g,i]pyrano[3,2-b][1,5]dioxacyclo undecine-9,17-dione (55). $^1$H NMR (300 MHz, CDCl$_3$) δ 3.37 (s, 3 H), 3.59 (dd, J = 9.6 Hz, J = 3.6 Hz, 1 H), 3.80 (d, J = 12.6 Hz, 1 H), 3.96 (t, J = 9.3 Hz, 1 H), 4.52 (d, J = 3.9 Hz, 1 H), 4.62 (d, J = 12.0 Hz, 1 H), 4.72 (d, J = 11.4 Hz, 1 H), 4.79 (d, J = 12.0 Hz, 1 H), 4.84 (d, J = 11.4 Hz, 1 H), 4.95 (t, J = 9.9 Hz, 1 H), 5.07-5.20 (m, 6 H), 5.61 (br, 1 H), 5.72 (br, 1 H), 5.77 (br, 2 H), 6.46 (s, 1 H), 6.68 (s, 1 H), 7.25-7.41 (m, 20 H) $^{13}$C NMR (75 MHz, CDCl$_3$) δ 55.61, 63.88, 66.79, 72.27, 73.94, 75.12, 75.50, 75.65, 79.36, 79.94, 98.87, 108.1, 108.6, 113.5, 114.7, 127.8-129.0(20), 129.9, 130.4, 135.9, 136.1, 136.7, 136.8, 138.0, 138.4, 147.4(2), 149.1, 149.2, 167.1, 168.2.

TABLE 2-continued

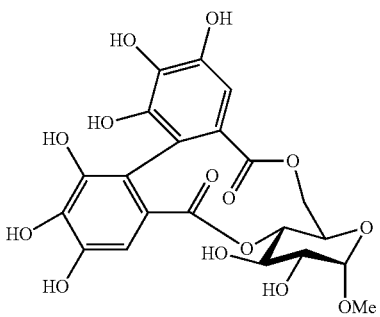

(11aR,13S,14R,15R,15aS)-2,3,4,5,6,7,14,15-octahydroxy-13-methoxy-11,11a,13,14,15,15a-hexahydrodibenzo[g,i]pyrano[3,2-b][1,5]dioxacycloundecine-9,17-dione(IA). $^1$H NMR (300 MHz, COCD6) δ 3.38 (s, 3 H), 3.55 (dd, J = 9.9 Hz, J = 3.3 Hz, 1 H), 3.72-3.82 (m, 2 H), 3.94 (s, 1 H), 4.13 (dd, J = 10.5 Hz, J = 7.2 Hz, 1 H), 4.70-4.80 (m, 2 H), 5.14 (dd, J = 12.9 Hz, J = 6.3 Hz, 1 H), 6.59 (s, 1 H), 6.59 (s, 1 H).

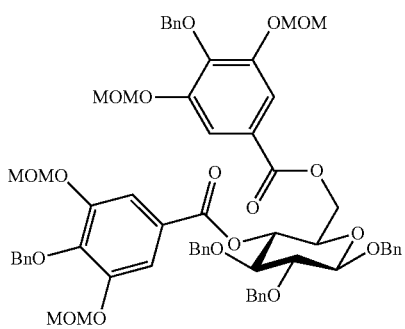

(2R,3R,4S,5R,6R)-4,5,6-tris(benzyloxy)-2-(((4-(benzyloxy)-3,5-bis(methoxymethoxy)benzoyl)oxy)methyl)tetrahydro-2H-pyran-3-yl4-(benzyloxy)-3,5-bis(methoxymethoxy) benzoate (53b). $^1$H NMR (300 MHz, CDCl$_3$) δ 3.45 (s, 12 H), 3.64 (t, J = 9.0 Hz, 1 H), 3.78 (t, J = 9.3 Hz, 1 H), 3,87 (t, J = 6.9 Hz, 1 H), 4.29 (dd, J = 12.3 Hz, J = 7.2 Hz, 1 H), 4.57-4.80 (m, 6 H), 4.93-4.98 (m, 2 H), 5.12-5.18 (m, 12 H), 5.28 (t, J = 9.9, 1 H), 7.08-7.56 (m, 29 H) $^{13}$C NMR (75 MHz, CDCl$_3$) δ 56.51(4), 63.97, 71.07, 71.60, 72.25, 75.04, 75.34, 75.37(2), 81.75, 82.10, 95.61(4), 102.1, 112.4(4), 125.0, 125.5, 127.6-128.7(25), 137.1, 137.4, 138.1, 138.4(2), 143.3, 143.4, 151.0(2), 151.1(2), 164.8, 165.7.

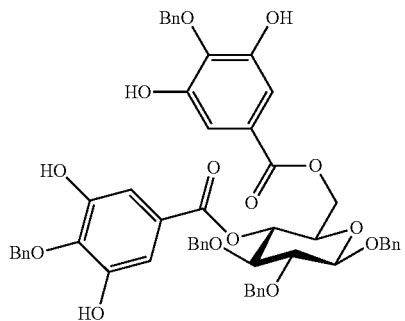

(2R,3R,4S,5R,6R)-4,5,6-tris(benzyloxy)-2-(((4-(benzyloxy)-3,5-dihydroxybenzoyl)oxy)methyl)tetrahydro-2H-pyran-3-yl4-(benzyloxy)-3,5-dihydroxybenzoate (54b). $^1$H NMR (300 MHz, CDCl$_3$) δ 3.51-3.80 (m, 3 H), 4.50 (t, J = 4.8 Hz, 1 H), 4.57-4.78 (m, 6 H), 4.95-5.00 (m, 2 H), 5.12-5.14 (d, 4 H), 5.39 (t, 9.3 Hz, 1 H), 6.23 (br, 4 H), 7.07-7.38 (m, 29 H) $^{13}$C NMR (75 MHz, CDCl$_3$) δ 63.42, 71.36, 71.43, 71.76, 75.20, 75.35(2), 75.56, 81.39, 82.24, 102.5, 110.1(4), 124.7, 125.0, 127.8-129.0(25), 136.8, 136.9, 137.1, 137.8, 137.9, 138.0, 138.3, 149.2(4), 165.8, 166.6.

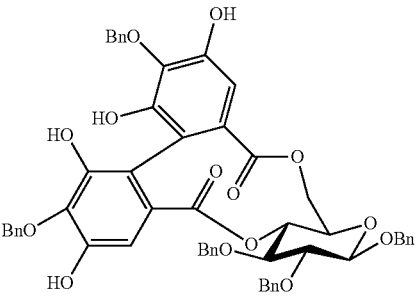

(11aR,13R,14R,15S,15aR)-3,6,13,14,15-pentakis(benzyloxy)-2,4,5,7-tetrahydroxy-11,11a,13,14,15,15a-hexahydrodibenzo[g,i]pyrano[3,2-b][1,5]dioxacycloundecine-9,17-dione(55b). $^1$H NMR (300 MHz, CDCl$_3$) δ 3.47-3.78 (m, 3 H), 3.98 (d, J = 12.9 Hz, 1 H), 4.55-5.00 (m, 8 H), 5.09-5.23 (m, 5 H), 5.84-6.19 (br, 4 H), 6.50 (s, 1 H), 6.68 (s, 1 H), 7.17-7.39 (m, 25 H) $^{13}$C NMR (75 MHz, CDCl$_3$) δ 63.83, 71.43, 71.64, 72.12, 74.91, 75.38, 75.67, 75.84, 81.35, 82.53, 103.2, 108.0, 108.8, 110.1, 113.2, 114.7, 127.9-129.1(25), 129.9, 130.6, 135.8, 136.1, 136.7, 137.2, 138.2(2), 147.3, 147.4, 149.2(2), 167.0, 168.0.

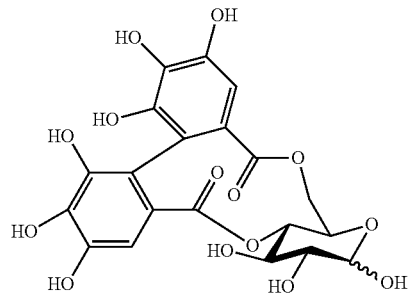

(11aR,14R,15R,15aS)-2,3,4,5,6,7,13,14,15-nonahydroxy-11,11a,13,14,15,15a-hexahydro dibenzo[g,i]pyrano[3,2-b][1,5]dioxacycloundecine-9,17-dione (IF). $^1$H NMR (300 MHz, CDCl$_3$) mixture of anomers 3:2 δ 3.41-3.94 (m, 4 H), 4.29-4.58 (m, 1 H), 4.82-4.85 (m, 1 H), 5.10-5.23 (m, 1 H), 6.56 (s, 0.6 H), 6.59 (s, 0.4 H), 6.67 (s, 0.6 H), 6.68 (s, 0.4 H).

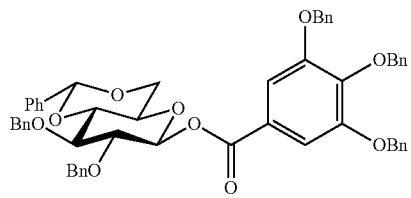

(2R,4aR,6S,7R,8S,8aR)-7,8-bis(benzyloxy)-2-phenylhexahydropyrano[3,2-d][1,3]dioxin-6-yl 3,4,5-tris(benzyloxy)benzoate [1]H (51c). NMR (300 MHz, CDCl$_3$) δ 3.66 (m, 5 H), 4.41 (dd, J = 9.9 Hz, J = 4.8 Hz, 1 H), 4.63 (J = 11.1 Hz, 1 H), 4.76 (d, J = 11.4 Hz, 1 H), 4.80 (d, J = 11.4 Hz, 1 H), 4.98 (d, J = 11.1 Hz, 1 H), 5.07 (m, 2 H), 5.11 (d, J = 4.5 Hz, 2 H), 5.17 (s, 2 H), 5.60 (s, 1 H), 5.96 (d, J = 7.8 Hz, 1 H), 7.17-7.53 (m, 32 H) $^{13}$C NMR (75 MHz, CDCl$_3$) δ 66.85, 68.72, 71.36(2), 75.26(2), 75.45, 80.80, 81.27, 81.46, 94.89, 101.4, 109.7(2), 124.0, 126.2(2), 129.2-127.5(28), 136.7(2), 137.3, 137.4, 137.8, 138.4, 143.2, 152.7(2), 164.3. m/z: 893 [M + Na]$^+$, 608, 568, 489; HRMS: calcd. for C$_{55}$H$_{50}$NaO$_{10}$: 893.3296 [M + Na]$^+$; found 893.3279.

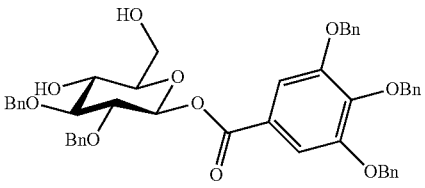

(2S,3R,4S,5R,6R)-3,4-bis(benzyloxy)-5-hydroxy-6-(hydroxymethyl)tetrahydro-2H-pyran-2-yl 3,4,5-tris(benzyloxy)benzoate (52c). $^1$H NMR (300 MHz, CDCl$_3$) δ 3.92-3.53 (m, 6 H), 4.67 (d, J = 2.4 Hz, TABLE 2-continued 2 H), 4.73 (d, J = 11.4 Hz, 1 H), 4.98 (d, J = 11.7 Hz, 1 H), 5.16-5.08 (m, 6 H), 5.89 (d, J = J = 7.8 Hz, 1 H), 7.19-7.42 (m, 27 H) $^{13}$C NMR (75 MHz, CDCl$_3$) δ 62.12, 70.05, 71.38(2), 75.16, 75.29, 75.54, 76.19, 81.05, 84.25, 94.94, 109.7(2), 124.1, 128.8-127.5(25), 136.7(2), 137.4, 137.8, 138.5, 143.2, 152.8(2), 164.5. m/z: 805 [M + Na]$^+$, 553, 441; HRMS: calcd. for C$_{48}$H$_{46}$NaO$_{10}$: 805.2983 [M + Na]$^+$; found 805.2986.

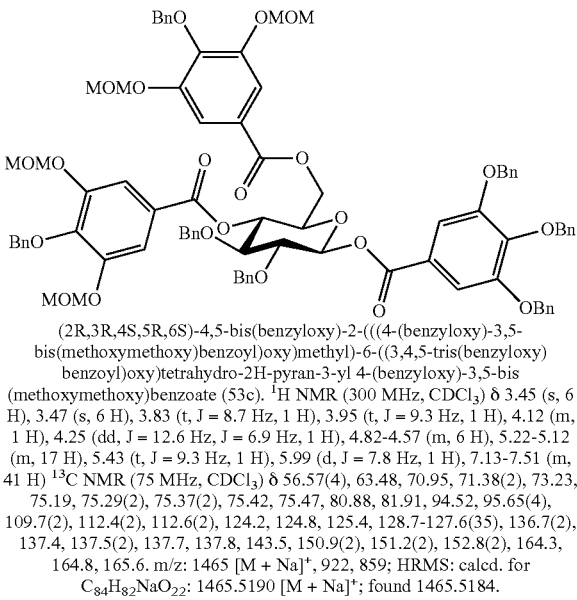

(2R,3R,4S,5R,6S)-4,5-bis(benzyloxy)-2-(((4-(benzyloxy)-3,5-bis(methoxymethoxy)benzoyl)oxy)methyl)-6-((3,4,5-tris(benzyloxy)benzoyl)oxy)tetrahydro-2H-pyran-3-yl 4-(benzyloxy)-3,5-bis(methoxymethoxy)benzoate (53c). $^1$H NMR (300 MHz, CDCl$_3$) δ 3.45 (s, 6 H), 3.47 (s, 6 H), 3.83 (t, J = 8.7 Hz, 1 H), 3.95 (t, J = 9.3 Hz, 1 H), 4.12 (m, 1 H), 4.25 (dd, J = 12.6 Hz, J = 6.9 Hz, 1 H), 4.82-4.57 (m, 6 H), 5.22-5.12 (m, 17 H), 5.43 (t, J = 9.3 Hz, 1 H), 5.99 (d, J = 7.8 Hz, 1 H), 7.13-7.51 (m, 41 H) $^{13}$C NMR (75 MHz, CDCl$_3$) δ 56.57(4), 63.48, 70.95, 71.38(2), 73.23, 75.19, 75.29(2), 75.37(2), 75.42, 75.47, 80.88, 81.91, 94.52, 95.65(4), 109.7(2), 112.4(2), 112.6(2), 124.2, 124.8, 125.4, 128.7-127.6(35), 136.7(2), 137.4, 137.7, 137.8, 143.5, 150.9(2), 151.2(2), 152.8(2), 164.3, 164.8, 165.6. m/z: 1465 [M + Na]$^+$, 922, 859; HRMS: calcd. for C$_{84}$H$_{82}$NaO$_{22}$: 1465.5190 [M + Na]$^+$; found 1465.5184.

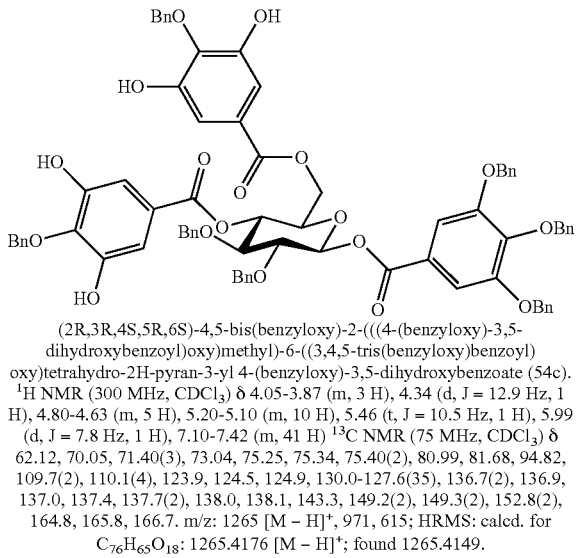

(2R,3R,4S,5R,6S)-4,5-bis(benzyloxy)-2-(((4-(benzyloxy)-3,5-dihydroxybenzoyl)oxy)methyl)-6-((3,4,5-tris(benzyloxy)benzoyl)oxy)tetrahydro-2H-pyran-3-yl 4-(benzyloxy)-3,5-dihydroxybenzoate (54c). $^1$H NMR (300 MHz, CDCl$_3$) δ 4.05-3.87 (m, 3 H), 4.34 (d, J = 12.9 Hz, 1 H), 4.80-4.63 (m, 5 H), 5.20-5.10 (m, 10 H), 5.46 (t, J = 10.5 Hz, 1 H), 5.99 (d, J = 7.8 Hz, 1 H), 7.10-7.42 (m, 41 H) $^{13}$C NMR (75 MHz, CDCl$_3$) δ 62.12, 70.05, 71.40(3), 73.04, 75.25, 75.34, 75.40(2), 80.99, 81.68, 94.82, 109.7(2), 110.1(4), 123.9, 124.5, 124.9, 130.0-127.6(35), 136.7(2), 136.9, 137.0, 137.4, 137.7(2), 138.0, 138.1, 143.3, 149.2(2), 149.3(2), 152.8(2), 164.8, 165.8, 166.7. m/z: 1265 [M − H]$^+$, 971, 615; HRMS: calcd. for C$_{76}$H$_{65}$O$_{18}$: 1265.4176 [M − H]$^+$; found 1265.4149.

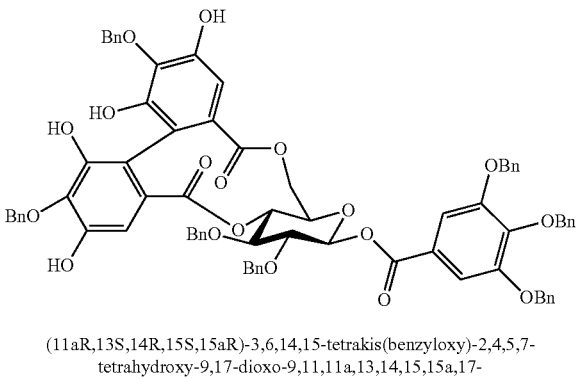

(11aR,13S,14R,15S,15aR)-3,6,14,15-tetrakis(benzyloxy)-2,4,5,7-tetrahydroxy-9,17-dioxo-9,11,11a,13,14,15,15a,17-octahydrodibenzo[g,i]pyrano[3,2-b][1,5]dioxacyclo undecin-13-yl 3,4,5-tris(benzyloxy)benzoate (55c). $^1$H NMR (300 MHz, CDCl$_3$) δ 3.52 (t, J = 5.4 Hz, 1 H), 4.03-3.75 (m, 4 H), 4.77-4.52 (m, 4 H), 5.24-5.08 (m, 11 H), 5.91 (d, J = 7.5 Hz, 1 H), 6.52 (s, 1 H), 6.67 (s, 1 H), 7.10-7.41 (m, 37 H) $^{13}$C NMR (75 MHz, CDCl$_3$) δ 63.59, 71.36, 71.48, 71.95, 72.33, 74.94, 75.23, 75.36, 75.74, 75.89, 81.35, 81.59, 94.69, 108.1, 108.8, 109.7(2), 113.1, 114.8, 124.0, 129.1-127.6(35), 129.7, 130.8, 135.8, 136.3, 136.7, 136.8(3), 137.5, 137.6, 138.0, 143.2, 147.4, 147.5, 149.2, 149.3, 152.8(2), 164.5, 167.1, 167.6. m/z: 1263 [M − H]$^+$, 855, 529; HRMS: calcd. for C$_{76}$H$_{63}$O$_{18}$: 1263.4020 [M − H]$^+$; found 1263.3999.

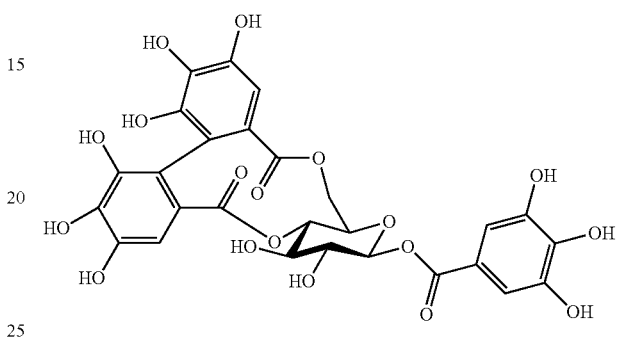

Strictinin (IC). m/z: 633 [M − H]$^+$, 498, 306; HRMS: calcd. for C$_{27}$H$_{21}$O$_{18}$: 633.0733 [M − H]$^+$; found 633.0752.

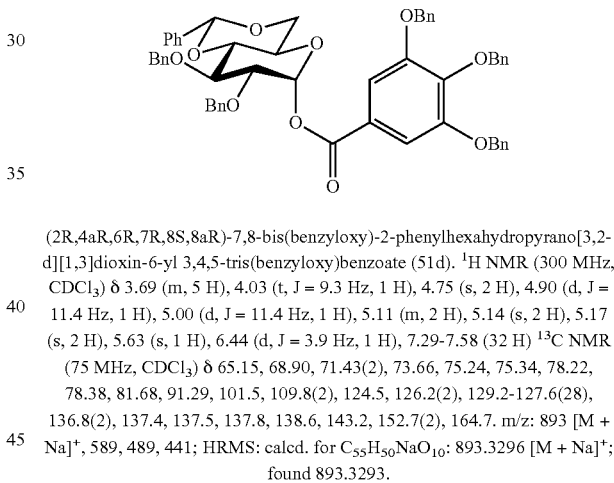

(2R,4aR,6R,7R,8S,8aR)-7,8-bis(benzyloxy)-2-phenylhexahydropyrano[3,2-d][1,3]dioxin-6-yl 3,4,5-tris(benzyloxy)benzoate (51d). $^1$H NMR (300 MHz, CDCl$_3$) δ 3.69 (m, 5 H), 4.03 (t, J = 9.3 Hz, 1 H), 4.75 (s, 2 H), 4.90 (d, J = 11.4 Hz, 1 H), 5.00 (d, J = 11.4 Hz, 1 H), 5.11 (m, 2 H), 5.14 (s, 2 H), 5.17 (s, 2 H), 5.63 (s, 1 H), 6.44 (d, J = 3.9 Hz, 1 H), 7.29-7.58 (32 H) $^{13}$C NMR (75 MHz, CDCl$_3$) δ 65.15, 68.90, 71.43(2), 73.66, 75.24, 75.34, 78.22, 78.38, 81.68, 91.29, 101.5, 109.8(2), 124.5, 126.2(2), 129.2-127.6(28), 136.8(2), 137.4, 137.5, 137.8, 138.6, 143.2, 152.7(2), 164.7. m/z: 893 [M + Na]$^+$, 589, 489, 441; HRMS: calcd. for C$_{55}$H$_{50}$NaO$_{10}$: 893.3296 [M + Na]$^+$; found 893.3293.

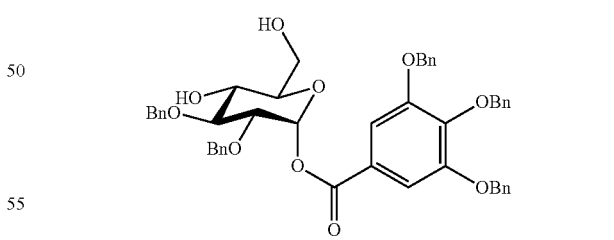

(2R,3R,4S,5R,6R)-3,4-bis(benzyloxy)-5-hydroxy-6-(hydroxymethyl)tetrahydro-2H-pyran-2-yl 3,4,5-tris(benzyloxy)benzoate (52d). 1H NMR (300 MHz, CDCl$_3$) δ 3.83-3.69 (m, 6 H), 4.78-4.64 (m, 3 H), 5.03 (d, J = 11.7 Hz, 1 H), 5.21-5.12 (m, 6 H) 6.49 (d, J = 3.3 Hz, 1 H), 7.44-7.27 (m, 27 H) $^{13}$C NMR (75 MHz, CDCl$_3$) δ 62.01, 69.58, 71.40(2), 73.00, 73.82, 75.27, 75.35, 78.93, 80.77, 90.74, 109.7(2), 124.6, 128.8-127.5(25), 136.7(2), 137.5, 137.6, 138.6, 143.2, 152.7(2), 164.7. m/z: 805 [M + Na]$^+$, 553, 441; HRMS: calcd. for C$_{48}$H$_{46}$NaO$_{10}$: 805.2983 [M + Na]$^+$; found 805.2983.

TABLE 2-continued

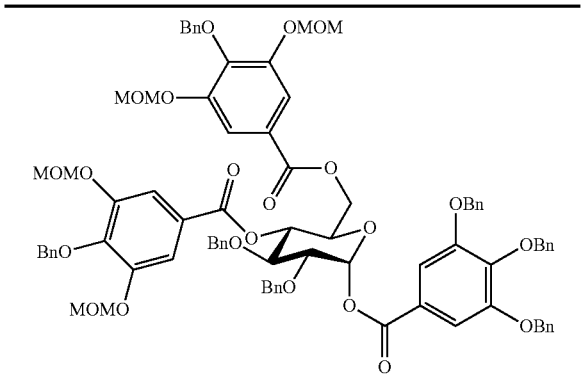

(2R,3R,4S,5R,6R)-4,5-bis(benzyloxy)-2-(((4-(benzyloxy)-3,5-bis(methoxymethoxy)benzoyl)oxy)methyl)-6-((3,4,5-tris(benzyloxy)benzoyl)oxy)tetrahydro-2H-pyran-3-yl4-(benzyloxy)-3,5-bis(methoxymethoxy)benzoate (53d). $^1$H NMR (300 MHz, CDCl$_3$) δ 3.41 (s, 6 H), 3.43 (s, 6 H), 3.89 (dd, J = 9.3 Hz, J = 3.6 Hz, 1 H), 4.13-4.33 (m, 3 H), 4.56 (d, J = 10.5 Hz, 1 H), 4.68-4.90 (m, 4 H), 5.08-5.20 (m, 18 H), 5.42 (t, J = 9.9 Hz, 1 H), 6.56 (d, J = 3.6 Hz, 1 H), 7.13-7.55 (m, 41 H) $^{13}$C NMR (75 MHz, CDCl$_3$) δ 56.49(4), 63.03, 70.57, 70.78, 71.33(2), 73.39(2), 75.34(5), 78.69, 78.97, 90.62, 95.55(2), 95.66(2), 109.7(2), 112.3(2), 112.5(2), 124.6, 124.9, 125.3, 128.8-127.5(35), 136.8(2), 137.3, 137.5, 137.6, 138.1, 143.1, 143.4, 150.9(2), 151.2(2), 152.6(2), 164.4, 164.8, 165.6. m/z: 1465 [M + Na]$^+$, 764; HRMS: calcd. for C$_{48}$H$_{46}$NaO$_{10}$: 1465.5190 [M + Na]$^+$; found 1465.5190.

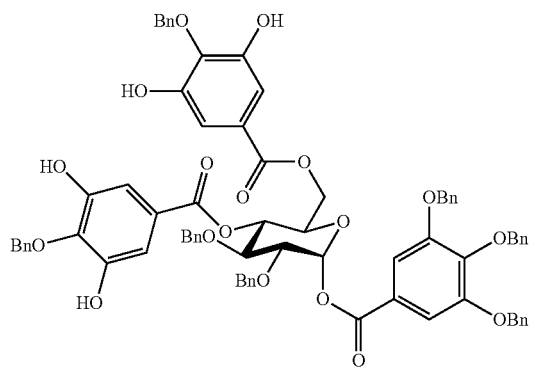

(2R,3R,4S,5R,6R)-4,5-bis(benzyloxy)-2-(((4-(benzyloxy)-3,5-dihydroxybenzoyl)oxy) methyl)-6-((3,4,5-tris(benzyloxy)benzoyl)oxy)tetrahydro-2H-pyran-3-yl 4-(benzyloxy)-3,5-dihydroxybenzoate (54d). $^1$H NMR (300 MHz, CDCl$_3$) δ 4.03-4.31 (m, 4 H), 4.72-4.88 (m, 5 H), 5.16-5.32 (m, 10 H), 5.44 (t, J = 10.2, 1 H), 6.61 (d, J = 3.6 Hz, 1 H), 7.16-7.53 (41 H) $^{13}$C NMR (75 MHz, CDCl$_3$) δ 62.27, 69.91, 70.50, 71.46(2), 73.52, 75.08, 75.20, 75.31, 75.42, 78.05, 78.34, 90.79, 109.8(2), 110.1(4), 124.5(2), 124.7, 130.0-127.6(35), 136.8(2), 136.9, 137.0, 137.5, 137.7, 137.8, 138.0, 138.1, 143.2, 149.2(2), 149.3(2), 152.8(2), 164.6, 165.9, 166.8. m/z: 1265 [M − H]$^+$, 615; HRMS: calcd. for C$_{76}$H$_{65}$O$_{18}$: 1265.4176 [M − H]$^+$; found 1265.4155.

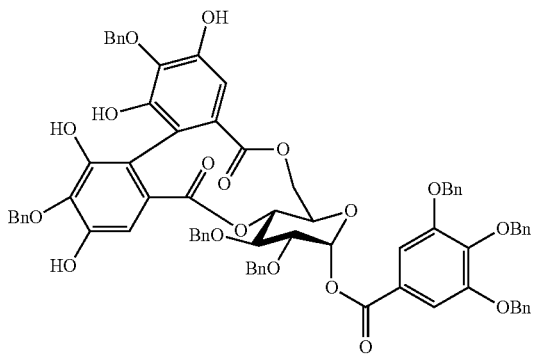

(11aR,13R,14R,15S,15aR)-3,6,14,15-tetrakis(benzyloxy)-2,4,5,7-tetrahydroxy-9,17-dioxo-9,11,11a,13,14,15,15a,17-octahydrodibenzo[g,i]pyrano[3,2-b][1,5]dioxacyclo undecin-13-yl 3,4,5-tris(benzyloxy)benzoate (55d). $^1$H NMR (300 MHz, CDCl$_3$) δ 3.71-4.00 (m, 5 H), 4.62-4.88 (m, 5 H), 5.00-5.24 (m, 10 H), 6.39 (d, J = 4.2 Hz, 1 H), 6.59 (s, 1 H), 6.71 (s, 1 H), 7.25-7.43 (m, 37 H) $^{13}$C NMR (75 MHz, CDCl$_3$) δ 63.42, 69.95, 71.36, 71.44(2), 73.64, 74.70, 75.40, 75.69, 75.88, 78.48, 79.29, 90.75, 107.7, 108.74, 109.8(2), 113.1, 114.9, 124.4, 129.1-127.4(35), 129.8, 130.8, 135.7, 136.1, 136.6, 136.7, 136.8(2), 137.5(2), 138.2, 143.1, 147.4, 147.5, 149.2, 149.4, 152.7(2), 164.4, 166.9, 167.5. m/z: 1287 [M + Na]$^+$, 922, 688; HRMS: calcd. for C$_{76}$H$_{64}$NaO$_{18}$: 1287.3985 [M + Na]$^+$; found 1287.3996.

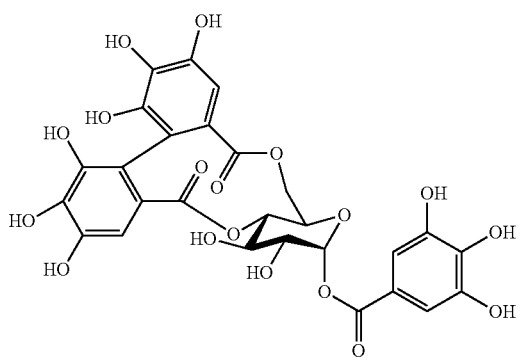

(11aR,13R,14R,15R,15aS)-2,3,4,5,6,7,14,15-octahydroxy-9,17-dioxo-9,11,11a,13,14,15,15a,17-octahydrodibenzo[g,i]pyrano[3,2-b][1,5]dioxacycloundecin-13-yl3,4,5-tri hydroxybenzoate (IG). $^1$H NMR (300 MHz, COCD$_6$) δ 3.72 (d, J = 13.2 Hz, 1 H), 3.88 (dd, J = 9.9 Hz, J = 4.2 Hz, 1 H), 4.08 (t, J = 9.3 Hz, 1 H), 4.41 (dd, J = 9.9 Hz, J = 6 Hz, 1 H), 4.91 (t, J = 9.3 Hz, 1 H), 5.19 (dd, J = 13.4 Hz, J = 6.6 Hz, 1 H), 6.35 (d, J = 4.2 Hz, 1 H), 6.60 (s, 1 H) 6.72 (s, 1 H), 7.19 (s, 2 H). m/z: 657 [M + Na]$^+$, 568, 454, 301; HRMS: calcd. for C$_{27}$H$_{22}$NaO$_{18}$: 657.0698 [M + Na]$^+$; found 657.0695.

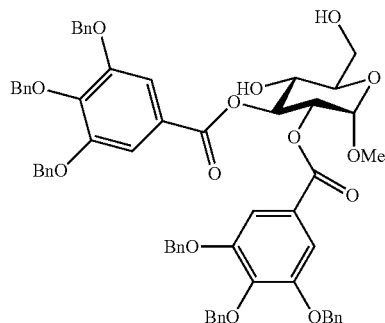

(2S,3R,4S,5R,6R)-5-hydroxy-6-(hydroxymethyl)-2-methoxytetrahydro-2H-pyran-3,4-diyl bis(3,4,5-tris(benzyloxy)benzoate) (52e). $^1$H NMR (300 MHz, CDCl$_3$) δ 3.46 (s, 3 H), 3.85-4.00 (m, 4 H), 4.94-5.04 (m, 12 H), 5.13-5.16 (m, 2 H), 5.69 (t, J = 9.9, 1 H), 7.22-7.39 (m, 34 H) $^{13}$C NMR (75 MHz, CDCl$_3$) δ 55.52, 62.03, 69.56, 71.10(2), 71.16(2), 71.57, 72.26, 74.68, 75.19(2), 97.23, 109.2(2), 109.3(2), 124.1, 124.3, 127.7-128.6(30), 136.5(2), 136.6(2), 137.4, 137.5, 142.9, 143.0, 152.6(4), 165.8, 167.1. m/z: 1061 [M + Na]$^+$, 715, 559; HRMS: calcd. for C$_{63}$H$_{58}$NaO$_{14}$: 1061.3719 [M + Na]$^+$; found 1061.3709.

TABLE 2-continued

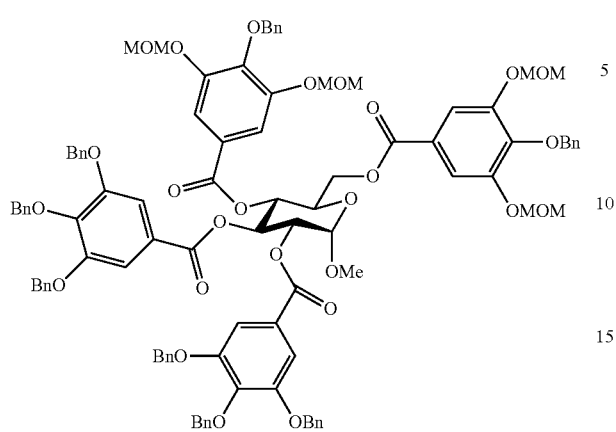

(2S,3R,4S,5R,6R)-5-((4-(benzyloxy)-3,5-bis(methoxymethoxy)benzoyl)oxy)-6-(((4-(benzyloxy)-3,5-bis(methoxymethoxy)benzoyl)oxy)methyl)-2-methoxytetrahydro-2H-pyran-3,4-diyl-bis(3,4,5-tris(benzyloxy)benzoate) (53e). $^1$H NMR (300 MHz, CDCl$_3$) δ 3.44 (s, 6 H), 3.48 (s, 6 H), 3.53 (s, 3 H), 4.43 (m, 2 H), 4.66 (d, J = 10.5 Hz, 1 H), 4.90-5.20 (m, 25 H), 5.32 (d, J = 3.3 Hz, 1 H), 5.63 (t, J = 9.9 Hz, 1 H), 6.13 (t, J = 9.9 Hz, 1 H), 7.19-7.47 (m, 46 H), 7.61 (s, 2 H) $^{13}$C NMR (75 MHz, CDCl$_3$) δ 55.66, 56.46(2), 56.53(2), 63.40, 67.50, 69.65, 71.14(3), 71.18(2), 72.78, 75.19, 75.22, 75.33, 75.34, 95.56(2), 95.58(2), 97.01, 109.1(2), 109.3(2), 112.4(2), 112.5(2), 124.2, 124.3, 124.4, 125.3, 127.7-128.7(40), 136.5(2), 136.7(2), 137.4, 137.4, 137.5(2), 142.9(2), 143.3, 143.9, 151.1(4), 152.6(4), 165.0, 165.5, 165.6, 165.7. m/z: 1721 [M + Na]$^+$, 872; HRMS: calcd. for C$_{99}$H$_{94}$NaO$_{26}$: 1721.5926 [M + Na]$^+$; found 1721.5916.

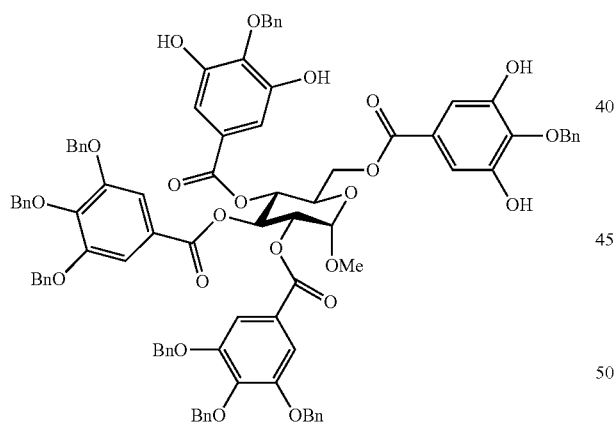

(2S,3R,4S,5R,6R)-5-((4-(benzyloxy)-3,5-dihydroxybenzoyl)oxy)-6-(((4-(benzyloxy)-3,5-dihydroxybenzoyl)oxy)methyl)-2-methoxytetrahydro-2H-pyran-3,4-diyl-bis(3,4,5-tris(benzyloxy)benzoate) (54e). $^1$H NMR (300 MHz, CDCl$_3$) δ 3.51 (s, 3 H), 4.40 (br, 2 H), 4.77-5.37 (m, 19 H), 5.65 (t, J = 9.9 Hz, 1 H), 5.87 (br, 4 H), 6.12 (t, J = 9.9 Hz, 1 H), 7.08-7.46 (m, 48 H). $^{13}$C NMR (75 MHz, CDCl$_3$) δ 55.91, 62.71, 67.94, 68.98, 71.16(2), 71.21(2), 72.86, 75.18, 75.24(2), 75.28(2), 97.30, 109.0(2), 109.4(2), 110.1(4), 124.1(2), 124.2, 124.6, 128.9-127.8(40), 136.4(2), 136.7(2), 136.8, 136.9, 137.4, 137.5, 138.1, 138.4, 142.9(2), 149.2(4), 152.7(4), 165.7, 165.8, 165.9, 166.6. m/z: 1545 [M + Na]$^+$, 955, 715, 489; HRMS: calcd. for C$_{91}$H$_{78}$NaO$_{22}$: 1545.4877 [M + Na]$^+$; found 1545.4832.

TABLE 2-continued

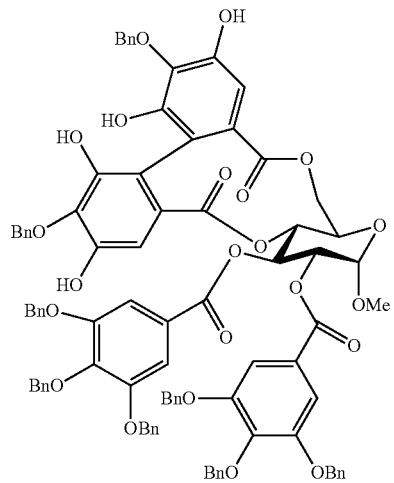

(11aR,13S,14R,15S,15aR)-3,6-bis(benzyloxy)-2,4,5,7-tetrahydroxy-13-methoxy-9,17-dioxo-9,11,11a,13,14,15,15a,17-octahydrodibenzo[g,i]pyrano[3,2-b][1,5]dioxacyclo undecine-14,15-diyl-bis(3,4,5-tris(benzyloxy)benzoate) (55e). $^1$H NMR (300 MHz, CDCl$_3$) δ 3.44 (s, 3 H), 3.97 (d, J = 12.9 Hz, 1 H), 4.45 (br, 1 H), 4.81-5.38 (m, 20 H), 5.94 (t, J = 10.2 Hz, 1 H), 6.70 (s, 1 H), 6.80 (s, 1 H), 7.14-7.45 (m, 44 H). $^{13}$C NMR (75 MHz, CDCl$_3$) δ 55.89, 63.46, 67.78, 70.49, 71.11, 71.22(2), 71.45, 72.94, 75.18, 75.24, 75.28, 75.65(2), 97.61, 108.2, 108.6, 109.4(4), 113.7, 114.0, 124.1, 124.2, 130.0-127.7(40), 129.7, 130.1, 136.0, 136.1, 136.6(3), 136.7(3), 137.5, 137.6, 142.9(2), 147.3, 147.5, 149.2, 149.3, 152.7(4), 165.7, 166.0, 167.0, 167.8. m/z: 1543 [M + Na]$^+$, 608; HRMS: calcd. for C$_{91}$H$_{76}$NaO$_{22}$: 1543.4720 [M + Na]$^+$; found 1545.4731.

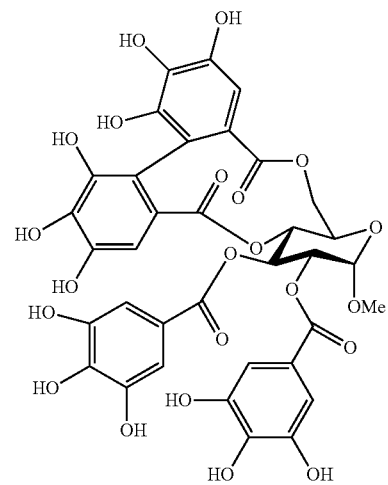

(11aR,13S,14R,15S,15aR)-2,3,4,5,6,7-hexahydroxy-13-methoxy-9,17-dioxo-9,11,11a,13,14,15,15a,17-octahydrodibenzo[g,i]pyrano[3,2-b][1,5]dioxacycloundecine-14,15-diyl-bis (3,4,5-trihydroxybenzoate) (IB). $^1$H NMR (300 MHz, COCD$_6$) δ 3.44 (s, 3 H), 3.86 (d, J = 14.7 Hz, 1 H), 4.40-4.47 (br, 1 H), 5.17-5.10 (m, 3 H), 5.33 (dd, J = 12.9 Hz, 6.6 Hz, 1 H), 5.82 (t, J = 10.2 Hz, 1 H), 6.44 (s, 1 H), 6.64 (s, 1 H) 6.98 (s, 2 H), 7.05 (s, 2 H). m/z: 823 [M + Na]$^+$, 552, 489, 413; HRMS: calcd. for C$_{35}$H$_{28}$NaO$_{22}$: 823.0964 [M + Na]$^+$; found 823.0952.

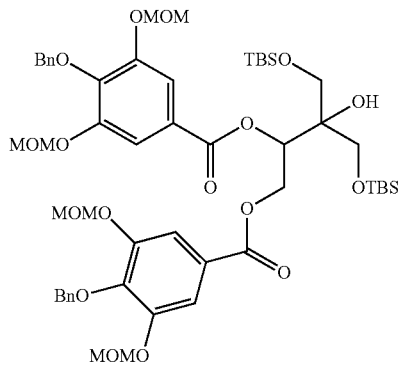

4-((tert-butyldimethylsilyl)oxy)-3-(((tert-butyldimethylsilyl)oxy)methyl)-3-hydroxy butane-1,2-diylbis(4-(benzyloxy)-3,5-bis(methoxymethoxy)benzoate) (66). $^1$H NMR (300 MHz, CDCl$_3$) δ 0.04 (s, 3 H), 0.07 (s, 3 H), 0.10 (s, 3 H), 0.11 (s, 3 H), 0.89 (s, 9 H), 0.92 (s, 9 H), 2.87 (br, 1 H), 3.43 (s, 6 H), 3.47 (s, 6 H), 3.61-3.80 (m, 4 H), 4.59 (dd, J = 12 Hz, J = 9.3 Hz, 1 H), 4.72 (dd, J = 12.3 Hz, J = 2.7 Hz, 1 H), 5.10-5.21 (m, 12 H), 5.69 (dd, J = 9.0 Hz, J = 2.1 Hz, 1 H), 7.30-7.56 (m, 14 H). $^{13}$C NMR (75 MHz, CDCl$_3$) δ 5.48(4), 18.31(2), 25.94(3), 25.96(3), 56.44(2), 56.46(2), 63.22, 63.35, 64.15, 73.35, 75.17, 75.28, 75.34, 95.49(2), 95.69(2), 112.3(2), 112.5(2), 125.5, 125.7, 128.2-128.5(10), 137.4, 137.5, 143.3(2), 150.9(2), 151.0(2), 165.2, 165.8.

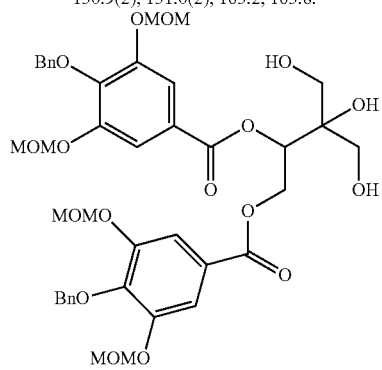

3,4-dihydroxy-3-(hydroxymethyl)butane-1,2-diylbis(4-(benzyloxy)-3,5-bis(methoxy methoxy)benzoate) (67). $^1$H NMR (300 MHz, CDCl$_3$) δ 3.42 (s, 6 H), 3.44 (s, 6 H), 3.71-3.89 (m, 5 H), 4.68 (dd, J = 12.0 Hz, J = 8.1 Hz, 1 H), 4.83 (dd, J = 12.3 Hz, J = 3.0 Hz, 1 H), 5.09-5.18 (m, 12 H), 5.63 (dd, J = 8.1 Hz, J = 2.7 Hz, 1 H), 7.28-7.52 (m, 14 H).

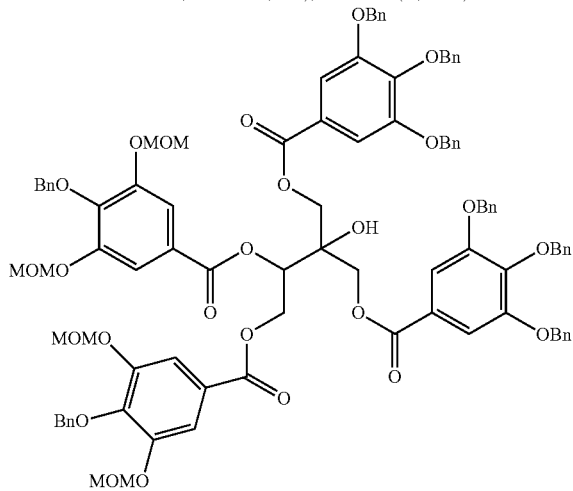

2-(1,2-bis((4-(benzyloxy)-3,5-bis(methoxymethoxy)benzoyl)oxy)ethyl)-2-hydroxy propane-1,3-diylbis(3,4,5-tris(benzyloxy)benzoate) (68). $^1$H NMR (300 MHz, CDCl$_3$) δ 2.71 (br, 1 H), 3.37 (s, 6 H), 3.44 (s, 6 H), 4.50-4.77 (m, 5 H), 4.94-5.21 (m, 25 H), 5.94 (d, J = 7.2 Hz, 2 H), 7.28-7.58 (m, 48 H).

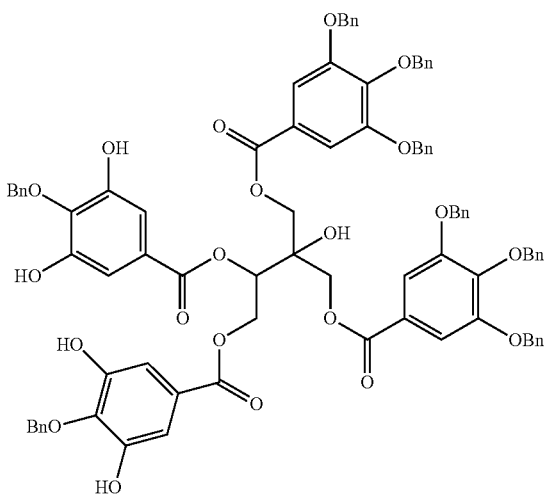 [SMILES: O=C(OCC(OC(=O)c1cc(O)c(OCc2ccccc2)c(O)c1)C(O)(COC(=O)c1cc(OCc2ccccc2)c(OCc2ccccc2)c(OCc2ccccc2)c1)COC(=O)c1cc(OCc2ccccc2)c(OCc2ccccc2)c(OCc2ccccc2)c1)c1cc(O)c(OCc2ccccc2)c(O)c1]

2-(1,2-bis((4-(benzyloxy)-3,5-dihydroxybenzoyl)oxy)ethyl)-2-hydroxypropane-1,3-diyl bis(3,4,5-tris(benzyloxy)benzoate) (69). $^1$H NMR (300 MHz, CDCl$_3$) δ 3.78 (br, 1 H), 4.53-4.91 (m, 6 H), 5.06-5.13 (m, 16 H), 5.90 (br, 5 H), 7.09-7.39 (m, 48 H).

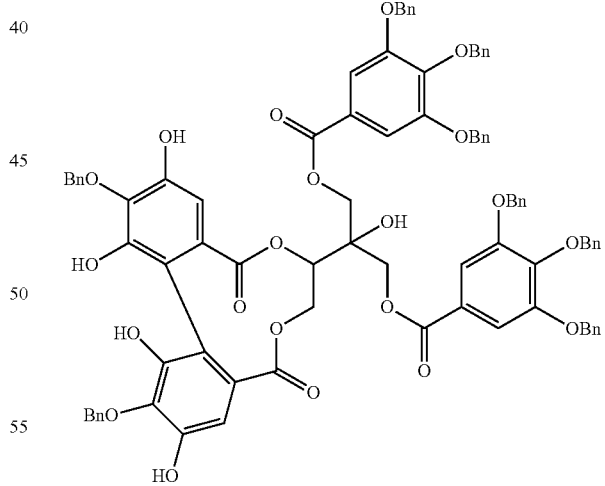

2-(2,13-bis(benzyloxy)-1,3,12,14-tetrahydroxy-5,10-dioxo-5,7,8,10-tetrahydrodibenzo [f,h][1,4]dioxecin-7-yl)-2-hydroxypropane-1,3-diylbis(3,4,5-tris(benzyloxy)benzoate) (70). $^1$H NMR (300 MHz, CDCl$_3$) δ 4.27 (m, 5 H), 4.69 (d, J = 11.1 Hz, 1 H), 5.06-5.14 (m, 16 H), 5.56 (d, J = 10.5 Hz, 1 H), 6.58 (s, 1 H), 6.71 (s, 1 H), 7.15-7.38 (m, 44 H).

TABLE 2-continued

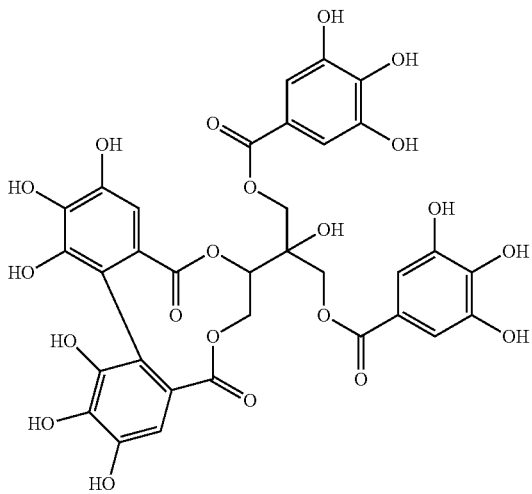 [SMILES: O=C(OCC(O)(COC(=O)c1cc(O)c(O)c(O)c1)C1COC(=O)c2cc(O)c(O)c(O)c2-c2c(cc(O)c(O)c2O)C(=O)O1)c1cc(O)c(O)c(O)c1]

2-(1,2,3,12,13,14-hexahydroxy-5,10-dioxo-5,7,8,10-tetrahydrodibenzo[f,h][1,4]dioxecin-7-yl)-2-hydroxypropane-1,3-diyl bis(3,4,5-trihydroxybenzoate) (II B). $^1$H NMR (300 MHz, COCD$_6$) δ 4.33 (dd, J = 10.8 Hz, 3.0 Hz, 1 H), 3.35-4.58 (m, 3 H), 5.13-5.18 (m, 1 H), 5.35 (t, J = 10.5 Hz, 1 H), 5.55 (dd, J = 10.8 Hz, 3.3 Hz, 1 H), 6.54 (s, 1 H), 6.62 (s, J = 1 H), 7.14-7.19 (m, 4 H).

II. Evaluation of anti-HIV Activity

A. Generation of HIV Stocks

Stocks of HIV-1 were generated by transfecting a 150 cm plate of 80% confluent HEK 293T cells with 75 μg of the HIV molecular clone pNL4-3 by using the CaPO$_4$ procedure of F. L. Graham et al., *J. Gen. Viol.*, 36, 59 (1977). Supernatants were collected at 48-h post-transfection, clarified to remove cell debris and frozen at −80° C. until needed. Virus production was assessed by reverse transcriptase activity in the viral stocks and by the single round of infection assay in HeLa37 cells described below. RT assays were performed as described by R. L. Wiley, *PNAS USA*, 83, 5038 (1986).

B. HIV-Infection Studies

All extracts or fractions were resuspended in DMSO. 2.5× 10$^2$ infectious particles of HIV (MOI=0.01) were combined with the concentrations of IA or IB noted in the figures. The amount of DMSO was adjusted so that equivalent concentrations of DMSO were used in all wells. No more than 0.5% DMSO was used, as HeLa37 cytotoxicity was observed at higher DMSO concentrations. The tannin and HIV mixture was added to 2.5×10$^4$ cells/well of HeLa37 cells in a 48-well format. The cells were maintained for 40 h at 37° C. in a CO$_2$ incubator. Cells were fixed in 75% acetone/25% water and immunostained for HIV antigens with human anti-HIV antisera (1:500) followed by HRP-conjugated goat anti-human IgG (1:500). 3-amino-9-ethyl-carbazole was used as the horse radish peroxidase substrate. Plates were dried and wells were counted for the number of HIV antigen-positive cells. Numbers of HIV antigen-positive cells in the presence of extract, fraction or fatty acid were divided by the number of HIV antigen-positive cells present in control wells that did not contain extracts, and these values are expressed as % control.

C. Cell-Viability Studies

HeLa37 cells were plated and treated with IA or IB as described above. Cell viability was monitored at 40 h after treatment initiation by ATPLite Assay (Packard Biosciences) per manufacturer's instructions.

D. Results

Figure 2:
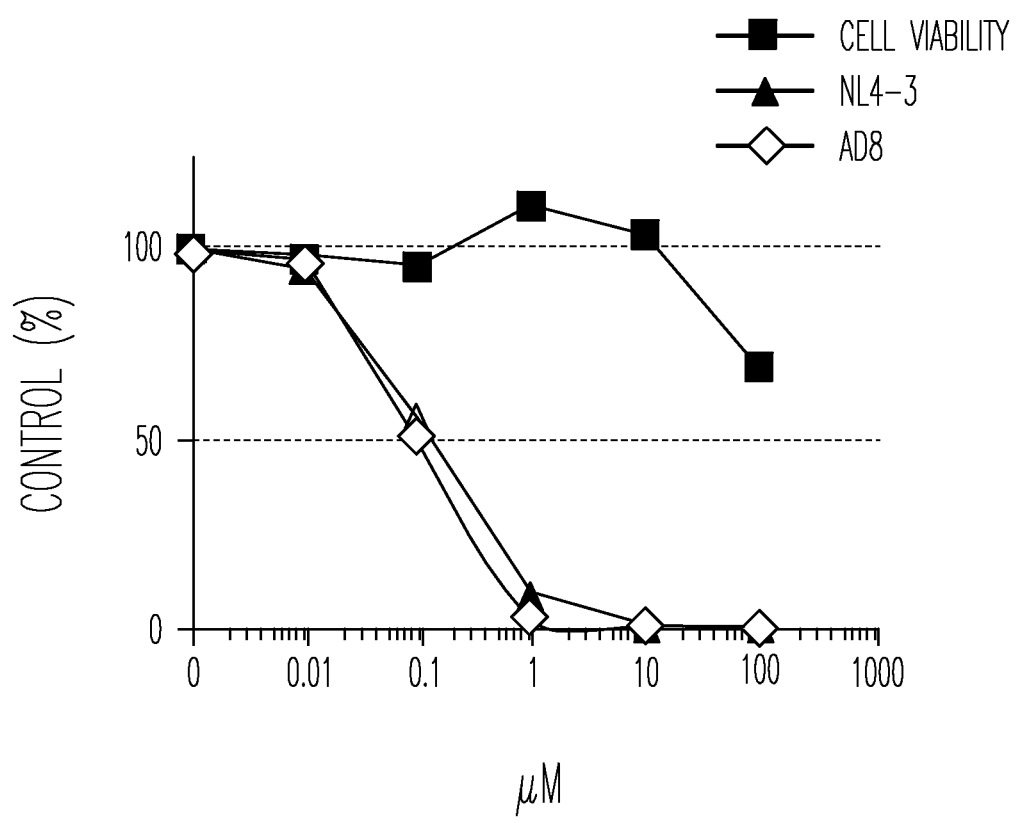

Tannins IA and IB have been evaluated for their anti-HIV activity. Both of these ellagitannins bear a hexahydroxydiphenoyl unit and one or two galloyl groups on the central glucose. Tannin IA had an IC$_{50}$ of about 0.11 μM with a CC$_{50}$ of ~100 μM for a TI of ~909 (FIG. 1). Tannin IB had an IC$_{50}$ of about 0.12 μM with a CC$_{50}$ of >100 μM for a TI of about 900 (FIG. 2). These latter two tannins have impressive therapeutic indices (>1100).

Furthermore, as shown in FIG. 2, tannin IB is effectively able to inhibit HIV strains of both CXCR4 (NL4-3) and CCR5 (AD8) tropism. Thus, both CCR5 and CXCR4 strains that are transmitted sexually are inhibited by IB. There are strains, that are frequently more virulent and evolve at latter stages of HIV infection, are inhibited by IB at equivalent concentrations. The ability of tannin IA to inhibit CCR5 tropic viruses has yet to be evaluated.

Figure 3:
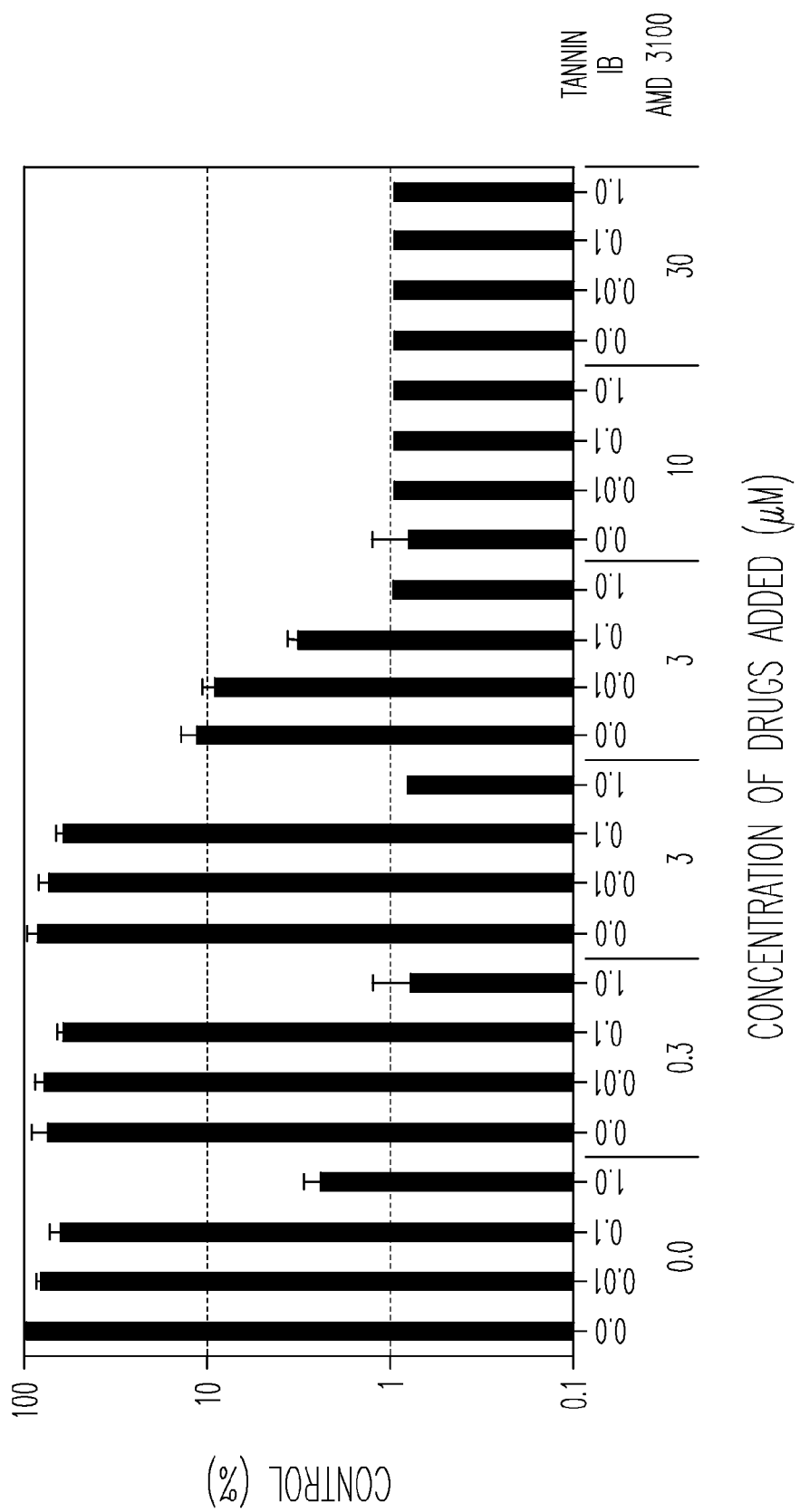
FIG. 3. Ability of the combination of tannin IB and a well established HIV inhibitor AMD3100 to enhance HIV inhibition.

The ability of compound IB to enhance the anti-HIV activity of a well established inhibitor of CXCR4 tropic viruses, AMD3100 (Perixafor) was assessed. The rationale behind this experiment is that HIV is able to rapidly evolve resistance to essentially all monotherapies, including AMD3100 and presumably compound IB. As a consequence, "cocktails" of antivirals are used in combination as antiviral therapies and cocktails of inhibitors are currently being developed for use as HIV microbicides. To determine if we observed enhancement of antiviral activity against the CXCR4 tropic HIV NL-4-3 in the presence of increasing concentrations of IB and AMD3100, doses bracketing the IC$_{50}$'s of both compounds were used (FIG. 3). At each concentration of AMD3100, a range of tannin IB doses were evaluated. As evident in the 3 μM concentration of AMD3100, increasing concentrations of tannin IB was able to enhance the antiviral activity of AMD3100 by more than a log. While more sophisticated analysis is required to determine if this enhancement is additive or synergistic, this simple experiment does provide evidence that the combination of compounds enhances their antiviral activity.

The present invention provides a method for the treatment of a viral infection, in particular an infection caused by a retrovirus such as HIV, in a mammal including man comprising administration of an effective amount of compounds of formulas (I), (II) or (III), or mixtures thereof.

There is also provided in a further or alternative aspect use of the present compounds for the manufacture of a medicament for the treatment of a viral infection.

The compounds of the invention is useful in the treatment of HIV infection broadly, including HIV/AIDS related conditions such as AIDS-related complex (ARC), progressive generalized lymphadenopathy (PGL), AIDS-related neurological conditions (such as dementia or tropical paraparesis), anti-HIV antibody positive and HIV-positive conditions, Kaposi's sarcoma, thrombocytopenia purpurea and associated opportunistic infections for example *Pneumocystis carinii*.

The compounds of the invention are also useful in the prevention of progression to clinical illness of individuals who are anti-HIV antibody or HIV-antigen positive and in prophylaxis following exposure to HIV.

The compounds may also be used for the prevention of viral contamination of physiological fluids such as blood or semen in vitro.

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 0.1 to about 750 mg/kg of bodyweight per day preferably in the range of 0.5 to 60 mg/kg/day, most preferably in the range of 1 to 20 mg/kg/day.

The desired dose may conveniently be presented in a single dose or as divided doses administered at appropriate intervals, for example as two, three, four or more sub-doses per day. Administration may be daily.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a bolus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention my be administered as the pure chemical it is preferable to formulate it into a pharmaceutical formulation.

The invention thus further provides a pharmaceutical formulation comprising at least one compound of the invention together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-linqual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and the, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compound according to the invention may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g., sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the compound(s) with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one more dispersing agents, solubilishing agents or suspending agents. Liquid sprays are conveniently delivered from pressurized packs.

For administration by inhalation a compound according to the invention is conveniently delivered from an insufflator, nebuliser or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compound according to the invention may take the form of a dry powder composition, for example a powder mix of the compound and a suitable powder base such a lactose or starch. The powder composition may be presented in unit dosage form in, for example, capsules or cartridges or, e.g., gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example other anti-infective agents. In particular the compounds of the invention may be employed together with known antiviral agents.

The invention thus provides, in a further aspect, a combination comprising the compound together with another therapeutically active agent, in particular an antiviral agent.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

Suitable therapeutic agents for use in such combination include acyclic nucleosides such as acyclovir or ganciclovir, interferons such as α, β or γ-interferon, renal excretion inhibitors such as probenecid, R5 inhibitors such as maraviroc, nucleoside transport inhibitors such as abacavir, dipyridamole, 2',3'-dideoxynucleosides such as AZT, 2',3'-dideoxycytidine, 2',3'-dideoxyadenosine, 2',3'-dideoxyinosine, 2',3'-dideoxythymidine, 2',3'-dideoxy-2',3'-didehydrothymidine and 2',3'-dideoxy-2',3'-didehydrocytidine, immunomodulators such as interleukin II (IL2) and granulocyte macrophage colony stimulating factor (GM-CSF), erythropoetin, ampligen, thymomodulin, thymopentin, foscarnet and ribavirin, integrase inhibitors, protease inhibitors and inhibitors of HIV binding to CD4 receptors, e.g., soluble CD4, CD4 fragments, CD4 hybrid molecules, glycosylation inhibitors such as 2-deoxy-D-glucose, castanospermine and 1-deoxynojirimycin, including AMD3100 and B4 and fusion inhibitors such as T20, C34 and T1249.

The individual components of such combinations may be administered either sequentially or simultaneously in separate or combined pharmaceutical formulations.

When the compound is used in combination with a second therapeutic agent active against the same virus the dose of each compound may be either the same as or differ from that when the compound is used alone.

All publications cited above are incorporated by reference herein as though fully set forth.

What is claimed is:

1. A method for treating HIV infection comprising administering to a subject afflicted with HIV infection an anti-HIV amount of a compound of formula (III):

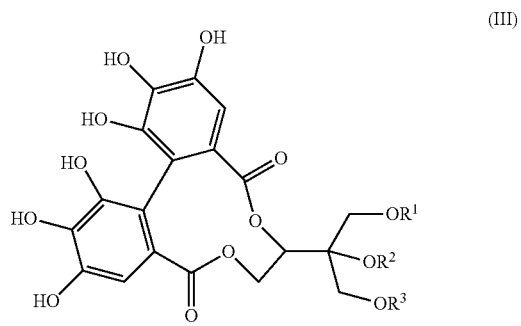

wherein $R^1$, $R^2$ and $R^3$ are individually H, $(C_1-C_4)$alkyl or galloyl (G), wherein at least one of $R^1$, $R^2$ or $R^3$ is G.

2. The method of claim 1 wherein $R^1$ and/or $R^3$ are G.

3. The method of claim 2 wherein $R^2$ is H.

* * * * *